US011007329B2

(12) United States Patent
Fischell et al.

(10) Patent No.: US 11,007,329 B2
(45) Date of Patent: May 18, 2021

(54) EXPANDABLE CATHETER SYSTEM FOR FLUID INJECTION INTO AND DEEP TO THE WALL OF A BLOOD VESSEL

(71) Applicant: ABLATIVE SOLUTIONS, INC., San Jose, CA (US)

(72) Inventors: David R. Fischell, Menlo Park, CA (US); Tim A. Fischell, Kalamazoo, MI (US)

(73) Assignee: ABLATIVE SOLUTIONS, INC., Wakefield, MA (US)

(*) Notice: Subject to any disclaimer, the term of this patent is extended or adjusted under 35 U.S.C. 154(b) by 0 days.

(21) Appl. No.: 16/178,940

(22) Filed: Nov. 2, 2018

(65) Prior Publication Data
US 2019/0167918 A1     Jun. 6, 2019

Related U.S. Application Data

(63) Continuation of application No. 14/738,776, filed on Jun. 12, 2015, now Pat. No. 10,118,004, which is a
(Continued)

(51) Int. Cl.
*A61F 5/40*     (2006.01)
*A61M 5/46*     (2006.01)
(Continued)

(52) U.S. Cl.
CPC .......... *A61M 5/46* (2013.01); *A61M 25/0026* (2013.01); *A61M 25/0084* (2013.01);
(Continued)

(58) Field of Classification Search
CPC ................ A61M 5/46; A61M 25/0084; A61M 2025/0085; A61M 2025/0086; A61M 2025/0087; A61B 5/6848; A61B 2018/044
See application file for complete search history.

(56) References Cited

U.S. PATENT DOCUMENTS 3,119,391 A    1/1964   Harrison
4,578,061 A    3/1986   Lemelson
(Continued)

FOREIGN PATENT DOCUMENTS

CN          1147964      4/1997
CN          1494399      5/2004
(Continued)

OTHER PUBLICATIONS

U.S. Appl. No. 15/940,178, filed Mar. 29, 2018, Fischell, et al.
(Continued)

*Primary Examiner* — Kami A Bosworth
(74) *Attorney, Agent, or Firm* — Knobbe, Martens, Olson & Bear, LLP

(57) ABSTRACT

A catheter-based/intravascular fluid injection system with application to renal denervation includes a multiplicity of needles which expand open around a central axis to engage the wall of a blood vessel, or the wall of the left atrium, allowing the injection of a cytotoxic and/or neurotoxic solution for ablating conducting tissue, or nerve fibers around the ostium of the pulmonary vein, or circumferentially in or just beyond the outer layer of the renal artery. The expandable delivery system includes expandable components that facilitate positioning of a multiplicity of injection needles against the inside wall of a blood vessel from where they can be advanced. The system also includes means to limit and/or adjust the depth of penetration of the ablative fluid into the tissue of the wall of the targeted blood vessel.

19 Claims, 22 Drawing Sheets

Related U.S. Application Data continuation of application No. 13/342,521, filed on Jan. 3, 2012, now Pat. No. 9,056,185, which is a continuation-in-part of application No. 13/294,439, filed on Nov. 11, 2011, now abandoned, and a continuation-in-part of application No. 13/216,495, filed on Aug. 24, 2011, now Pat. No. 9,278,196.

(51) Int. Cl.
  *A61M 25/00* (2006.01)
  *A61M 25/06* (2006.01)
  *A61B 5/00* (2006.01)

(52) U.S. Cl.
  CPC .... *A61M 25/0097* (2013.01); *A61M 25/0662* (2013.01); *A61B 5/6848* (2013.01); *A61M 2025/0039* (2013.01); *A61M 2025/0085* (2013.01); *A61M 2025/0086* (2013.01); *A61M 2025/0681* (2013.01); *A61M 2202/0007* (2013.01); *A61M 2205/0266* (2013.01); *A61M 2210/12* (2013.01)

(56) References Cited

U.S. PATENT DOCUMENTS

| | | |
|---|---|---|
| 4,798,595 A | 1/1989 | Anderson et al. |
| 5,304,141 A | 4/1994 | Johnson et al. |
| 5,354,279 A | 10/1994 | Hofling |
| 5,385,562 A | 1/1995 | Adams et al. |
| 5,405,376 A | 4/1995 | Mulier et al. |
| 5,419,777 A | 5/1995 | Hofling |
| 5,431,649 A * | 7/1995 | Mulier ............... A61B 18/1492 606/41 |
| 5,464,395 A | 11/1995 | Faxon et al. |
| 5,474,102 A | 12/1995 | Lopez |
| 5,551,426 A | 9/1996 | Hummel et al. |
| 5,588,960 A * | 12/1996 | Edwards ............ A61B 17/0625 604/20 |
| 5,667,488 A | 9/1997 | Lundquist et al. |
| 5,672,173 A | 9/1997 | Gough |
| 5,683,384 A | 11/1997 | Gough |
| 5,713,863 A | 2/1998 | Vigil et al. |
| 5,792,094 A | 8/1998 | Stevens et al. |
| 5,800,379 A | 9/1998 | Edwards |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,597 B1 | 5/2001 | Deem et al. |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,416,510 B1 | 7/2002 | Altman et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,599,267 B1 | 7/2003 | Ray et al. |
| 6,652,517 B1 | 11/2003 | Hall et al. |
| 6,685,648 B2 | 2/2004 | Flaherty et al. |
| 6,692,466 B1 | 2/2004 | Chow et al. |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,094,202 B2 | 8/2006 | Nobis et al. |
| 7,162,303 B2 | 1/2007 | Levin et al. |
| 7,181,288 B1 | 2/2007 | Rezai et al. |
| 7,273,469 B1 | 9/2007 | Chan et al. |
| 7,326,238 B1 | 2/2008 | Kilpatrick |
| 7,472,705 B2 | 1/2009 | Baran |
| 7,617,005 B2 | 11/2009 | Demarais et al. |
| 7,621,945 B2 | 11/2009 | Lennox et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |
| 8,088,127 B2 | 1/2012 | Mayse et al. |
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 | 4/2012 | Chan et al. |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,880,186 B2 | 11/2014 | Levin et al. |
| 8,934,978 B2 | 1/2015 | Deem et al. |
| 8,948,865 B2 | 2/2015 | Zarins et al. |
| 8,975,233 B2 | 3/2015 | Stein et al. |
| 8,979,801 B2 | 3/2015 | Lamson et al. |
| 8,983,595 B2 | 3/2015 | Levin et al. |
| 9,011,879 B2 | 4/2015 | Seward |
| 9,056,185 B2 | 6/2015 | Fischell et al. |
| 9,125,661 B2 | 9/2015 | Deem et al. |
| 9,131,978 B2 | 9/2015 | Zarins et al. |
| 9,131,983 B2 | 9/2015 | Fischell et al. |
| 9,138,281 B2 | 9/2015 | Zarins et al. |
| 9,179,962 B2 | 11/2015 | Fischell et al. |
| 9,192,715 B2 | 11/2015 | Gelfand et al. |
| 9,199,065 B2 | 12/2015 | Seward |
| 9,237,925 B2 | 1/2016 | Fischell et al. |
| 9,254,360 B2 | 2/2016 | Fischell et al. |
| 9,265,558 B2 | 2/2016 | Zarins et al. |
| 9,278,196 B2 | 3/2016 | Fischell et al. |
| 9,289,255 B2 | 3/2016 | Deem et al. |
| 9,301,795 B2 | 4/2016 | Fischell et al. |
| 9,308,044 B2 | 4/2016 | Zarins et al. |
| 9,314,630 B2 | 4/2016 | Levin et al. |
| 9,320,561 B2 | 4/2016 | Zarins et al. |
| 9,320,850 B2 | 4/2016 | Fischell et al. |
| 9,326,817 B2 | 5/2016 | Zarins et al. |

(56) References Cited

U.S. PATENT DOCUMENTS

| | | |
|---|---|---|
| 9,439,726 B2 | 9/2016 | Zarins et al. |
| 9,456,869 B2 | 10/2016 | Zarins et al. |
| 9,474,563 B2 | 10/2016 | Zarins et al. |
| 9,486,270 B2 | 11/2016 | Zarins et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,629,675 B2 | 4/2017 | Kleshinski et al. |
| 9,636,174 B2 | 5/2017 | Zarins et al. |
| 9,675,413 B2 | 6/2017 | Deem et al. |
| 9,743,983 B2 | 8/2017 | Levin et al. |
| 9,757,192 B2 | 9/2017 | Levin et al. |
| 9,789,276 B2 | 10/2017 | Seward et al. |
| 9,795,441 B2 | 10/2017 | Fischell et al. |
| 9,814,873 B2 | 11/2017 | Zarins et al. |
| 9,895,195 B2 | 2/2018 | Zarins et al. |
| 9,907,611 B2 | 3/2018 | Levin et al. |
| 9,931,046 B2 | 4/2018 | Fischell et al. |
| 9,949,652 B2 | 4/2018 | Fischell et al. |
| 9,993,278 B2 | 6/2018 | Rioux et al. |
| 10,022,059 B2 | 7/2018 | Fischell et al. |
| 10,118,004 B2 | 11/2018 | Fischell et al. |
| 10,172,663 B2 | 1/2019 | Fischell et al. |
| 10,226,278 B2 | 3/2019 | Fischell et al. |
| 10,350,392 B2 | 7/2019 | Fischell et al. |
| 10,405,912 B2 | 9/2019 | Fischell et al. |
| 10,420,481 B2 | 9/2019 | Fischell et al. |
| 10,485,951 B2 | 11/2019 | Fischell et al. |
| 10,517,666 B2 | 12/2019 | Fischell et al. |
| 10,576,246 B2 | 3/2020 | Fischell et al. |
| 10,736,524 B2 | 8/2020 | Fischell et al. |
| 10,736,656 B2 | 8/2020 | Fischell et al. |
| 10,849,685 B2 | 12/2020 | Denison et al. |
| 10,881,312 B2 | 1/2021 | Fischell et al. |
| 10,881,458 B2 | 1/2021 | Fischell et al. |
| 2001/0037065 A1 | 11/2001 | Graf et al. |
| 2002/0010439 A1 | 1/2002 | Miller |
| 2002/0052577 A1 | 5/2002 | Shimazaki |
| 2002/0082584 A1 | 6/2002 | Rosenman et al. |
| 2002/0120238 A1 | 8/2002 | McGuckin et al. |
| 2002/0151866 A1 | 10/2002 | Lundkvist et al. |
| 2002/0177846 A1 | 11/2002 | Mulier et al. |
| 2002/0183738 A1 | 12/2002 | Chee et al. |
| 2003/0009095 A1 | 1/2003 | Skarda |
| 2003/0032929 A1 | 2/2003 | McGuckin, Jr. |
| 2003/0171723 A1 | 9/2003 | Ponzi |
| 2004/0064098 A1 | 4/2004 | Cuschieri et al. |
| 2004/0133154 A1 | 7/2004 | Flaherty et al. |
| 2004/0147902 A1 | 7/2004 | McGuckin, Jr. et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0224118 A1 | 10/2006 | Morris et al. |
| 2006/0271111 A1 | 11/2006 | Demarais et al. |
| 2006/0271135 A1 | 11/2006 | Minar et al. |
| 2007/0005018 A1 | 1/2007 | Tekbuchava |
| 2007/0060812 A1 | 3/2007 | Harel et al. |
| 2007/0083239 A1 | 4/2007 | Demarias et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0185483 A1 | 8/2007 | Butty et al. |
| 2007/0203549 A1 | 8/2007 | Demarais et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0039786 A1 | 2/2008 | Epstein et al. |
| 2008/0045890 A1 | 2/2008 | Seward et al. |
| 2008/0051756 A1 | 2/2008 | Makower et al. |
| 2008/0125709 A1* | 5/2008 | Chang .................. A61M 29/00 604/96.01 |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0305546 A1 | 12/2010 | Seward et al. |
| 2010/0324446 A1 | 12/2010 | Pendleton |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0172593 A1 | 7/2011 | Lyyikainen et al. |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2011/0295354 A1 | 12/2011 | Bueche et al. |
| 2012/0010524 A1 | 1/2012 | Fojtik et al. |
| 2012/0041419 A1 | 2/2012 | Blanchard et al. |
| 2012/0053604 A1 | 3/2012 | DiCaprio |
| 2012/0071832 A1 | 3/2012 | Bunch |
| 2012/0083877 A1 | 4/2012 | Nguyen et al. |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0024959 A1 | 1/2014 | Sobotka |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0127126 A1 | 5/2014 | Lifton et al. |
| 2014/0236103 A1 | 8/2014 | Fischell et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1 | 4/2015 | Fischell et al. |
| 2015/0119875 A1 | 4/2015 | Fischell et al. |

(56) References Cited

U.S. PATENT DOCUMENTS

| | | |
|---|---|---|
| 2015/0126965 A1 | 5/2015 | Liungman |
| 2015/0132409 A1 | 5/2015 | Stein et al. |
| 2015/0202220 A1 | 7/2015 | Stein et al. |
| 2015/0224289 A1 | 8/2015 | Seward |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0279384 A1 | 9/2016 | Zarins et al. |
| 2016/0338734 A1 | 11/2016 | Shah et al. |
| 2016/0354137 A1 | 12/2016 | Fischell et al. |
| 2017/0119408 A1 | 5/2017 | Ma |
| 2017/0119974 A1 | 5/2017 | Racz |
| 2017/0304594 A1 | 10/2017 | Fischell et al. |
| 2017/0326363 A1 | 11/2017 | Deem et al. |
| 2017/0332926 A1 | 11/2017 | Fischell et al. |
| 2018/0043107 A1 | 2/2018 | Hooven et al. |
| 2018/0071019 A1 | 3/2018 | Fischell et al. |
| 2018/0085554 A1 | 3/2018 | Kassab et al. |
| 2018/0193596 A1 | 7/2018 | Fischell et al. |
| 2018/0279894 A1 | 10/2018 | Fischell et al. |
| 2019/0008580 A1 | 1/2019 | Fischell et al. |
| 2019/0015002 A1 | 1/2019 | Fischell et al. |
| 2019/0076186 A1 | 3/2019 | Fischell et al. |
| 2019/0076187 A1 | 3/2019 | Fischell et al. |
| 2019/0076188 A1 | 3/2019 | Fischell et al. |
| 2019/0117936 A9 | 4/2019 | Fischell et al. |
| 2019/0167918 A1 | 6/2019 | Fischell et al. |
| 2019/0201070 A1 | 7/2019 | Fischell et al. |
| 2019/0269435 A1 | 9/2019 | Fischell et al. |
| 2020/0022751 A1 | 1/2020 | Fischell et al. |
| 2020/0061348 A1 | 2/2020 | Fischell et al. |
| 2020/0163566 A1 | 5/2020 | Fischell et al. |
| 2020/0188007 A1 | 6/2020 | Fischell et al. |
| 2020/0197079 A1 | 6/2020 | Fischell et al. |
| 2020/0197663 A1 | 6/2020 | Fischell et al. |
| 2020/0269015 A1 | 8/2020 | Fischell et al. |

FOREIGN PATENT DOCUMENTS

| | | |
|---|---|---|
| CN | 1927130 | 3/2007 |
| EP | 0 797 409 | 10/1997 |
| EP | 0834288 | 4/1998 |
| EP | 0876805 | 8/2006 |
| JP | H06-277294 | 10/1994 |
| JP | H07509389 | 10/1995 |
| JP | H0889582 | 4/1996 |
| JP | 2001527428 | 12/2001 |
| JP | 2002510229 | 4/2002 |
| JP | 2002542901 | 12/2002 |
| JP | 2003-510126 | 3/2003 |
| JP | 2004-505689 | 2/2004 |
| JP | 2004516042 | 6/2004 |
| JP | 2005-40599 | 2/2005 |
| JP | 2008506500 | 3/2008 |
| JP | 09509865 | 3/2009 |
| JP | 2013-517847 | 5/2013 |
| WO | WO 94/04220 | 3/1994 |
| WO | WO 95/13752 | 5/1995 |
| WO | WO 2004/030740 | 4/2004 |
| WO | WO 2007/121143 | 10/2007 |
| WO | WO 2009/137819 | 11/2009 |
| WO | WO 2009/141727 | 11/2009 |
| WO | WO 2010/124120 | 10/2010 |
| WO | WO 2011/094367 | 8/2011 |
| WO | WO 2012/145300 | 10/2012 |
| WO | WO 2012/145304 | 10/2012 |
| WO | WO 2013/028781 | 2/2013 |
| WO | WO 2013/112844 | 8/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |
| WO | WO 2019/195625 | 10/2019 |

OTHER PUBLICATIONS

U.S. Appl. No. 15/947,460, filed Apr. 6, 2018, Fischell, et al.
U.S. Appl. No. 15/947,618, filed Apr. 6, 2018, Fischell, et al.
U.S. Appl. No. 15/947,619, filed Apr. 6, 2018, Fischell, et al.
U.S. Appl. No. 15/947,626, filed Apr. 6, 2018, Fischell, et al.
U.S. Appl. No. 16/034,854, filed Jul. 13, 2018, Fischell, et al.
U.S. Appl. No. 16/039,234, filed Jul. 18, 2018, Fischell, et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure and Autonomic Responses to Electrical Stimulation of the Renal Arterial Nerves Before and After Ablation of the Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Demas et al., Novel method for localized, functional sympathetic nervous system denervation of peripheral tissue using guanethidine (Journal of Neuroscience Methods 112, 2001), p. 21-28.
Dorward et al., "Reflex Responses to Baroreceptor, Chemoreceptor and Nociceptor Inputs in Single Renal Sympathetic Neurons in the Rabbit and the Effects of Anaesthesia on Them", Journal of the Autonomic Nervous System, 1987, vol. 18, p. 39-54.
F Mahoud, C Ukena, RE Schmieder. Ambulatory Blood Pressure Changes After Renal Sympathetic Denervation in Patients With Resistant Hypertension. Jul. 8, 2013 AHA Circulation 2013;128:132-140.
Gado et al., "Intra-articular guanethidine injection for resistant shoulder pain: a preliminary double blind study of a novel approach" Annals of the Rheumatic Disease, 1996, p. 199-201.
Habara et al., "Novel Use of a Local Drug Delivery Catheter for Coronary Perforation", Journal of Invasive Cardiology, Jan. 2011, vol. 23, No. 1, p. 1-8.
Hamza et al., "Substantial Reduction in Single Sympathetic Nerve Firing After Renal Denervation in Patients With Resistant Hypertension", Nov. 19, 2012, p. 856-864.
Hsu et al., "The Use of Intravenous Guanethidine Block in the Management of Reflex Sympathtic Dystrophy Syndrome of the Hand." Second Congress of the Hong Kong Orthopaedic Association, Nov. 1982, p. 93-105.
Hering et al., "Substantial Reduction in Single Sympathetic Nerve Firing After Renal Denervation in Patients With Resistant Hypertension", Nov. 19, 2012 in 15 pages.
Klein et al. "Functional reinnervation and development of supersensitivity to NE after renal denervation in rats" American Physiological Society, 1980, p. 353-358.
Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.
Markovic, B., et al., "Embolization With Absolute Ethanol Injection of Insufficiently Ligated Renal Artery After Open Nephrectomy"; Diagnostic and Interventional Radiology, Mar. 2011; vol. 17, Issue 1, p. 88-91.
"Multi-prong Infusion Needle Case Study", from the web site of peridot™ Precision Manufacturing, http://www.peridotcorp.com/casestudy.aspx, Copyright 2012, in 8 pages.
Nanni et al., Control of Hypertension by Ethanol Renal Ablation (Radiology 148:51-54, Jul. 1983), p. 52-54.
National Institute for Health and Care Excellence. Hypertension in adults: diagnosis and management. Aug. 24, 2011, NICE, CG127.

(56) References Cited

OTHER PUBLICATIONS

Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S, Jun. 2011.
Roytta et al., Taxol-induced neuropathy: short-term effects of local injection (Journal of Neurocytology 13, 1984), p. 685-701.
S.J. .Doletskiy et al. "Vysokochastotnaj Elektrotekhnika", M., 7-10 "Meditsina", 1980, p. 48-50, fig. 18-19.
Trostel et al., Do renal nerves chronically influence renal function and arterial pressure in spinal rats? (The American Physiological Society 1992), p. 1265-1270.
Verloop et al., Eligibility for percutaneous renal denervation: the importance of a systematic screening, Journal of Hypertension, 2013, p. 1-7.
Vink et al. Limited destruction of renal nerves after catheter-based renal denervation: results of a human case study, Nephrol Dial Transplant, 2014, p. 1-3.
YA Ashram, NH Abdel Wahab, IH Diab, Non-dipping pattern of nocturnal blood pressure in obstructive sleep apnea syndrom: Possible role of oxidative stress and endothelin-1 precursor. Feb. 14, 2013, Alexandria Journal of Medicine, 49, 153-161.
Zafonte et al., "Phenol and Alcohol Blocks for the Treatment of Spasticity", Physical medicine and rehabilitation clinics of North America, Nov. 2001, p. 817-832.
International Search Report and Written Opinion in PCT/US12/051906 dated Nov. 16, 2012 in 38 pages.
Extended Search Report in EP 12826228 dated Mar. 17, 2015 in 5 pages.
Office Action for Chinese Patent Application 201280051666.9 dated Sep. 22, 2015 in 9 pages.
Office Action for Japanese Patent Application 2014-527272 dated May 17, 2016 in 3 pages.
Office Action for Singapore Patent Application 11201400138Y dated Jun. 2, 2016 in 4 pages.
Office Action for Chinese Patent Application 201280051666.9 dated Jul. 15, 2016 in 7 pages.
Office Action for Chinese Patent Application 201280051666.9 dated Dec. 20, 2016 in 3 pages.
EPO Communication in EP 12826228 dated Mar. 31, 2017 in 4 pages.
Office Action for Japanese Patent Application 2014-527272 dated Apr. 3, 2017 in 6 pages.
Office Action for Chinese Patent Application 201280051666.9 dated Oct. 9, 2017 in 2 pages.
Office Action for Japanese Patent Application 2014-527272 dated Nov. 20, 2017 in 3 pages.
Office Action for Japanese Patent Application 2017-149730 dated Aug. 27, 2018 in 4 pages.
Office Action for Japanese Patent Application 2017-149730 dated Jul. 10, 2019 in 4 pages.
Office Action for Chinese Patent Application 201711417679.4 dated Feb. 19, 2020 in 17 pages.
U.S. Appl. No. 16/238,780, filed Jan. 3, 2019, Fischell, et al.
U.S. Appl. No. 16/296,688, filed Mar. 8, 2019, Fischell, et al.
U.S. Appl. No. 16/805,033, filed Feb. 28, 2020, Fischell et al.
U.S. Appl. No. 16/945,077, filed Jul. 31, 2020, Fischell et al.
U.S. Appl. No. 16/984,671, filed Aug. 4, 2020, Fischell et al.
U.S. Appl. No. 16/984,690, filed Aug. 4, 2020, Fischell et al.
U.S. Appl. No. 17/101,729, filed Nov. 23, 2020, Denison et al.
U.S. Appl. No. 17/127,151, filed Dec. 18, 2020, Fischell et al.
U.S. Appl. No. 17/127,443, filed Dec. 18, 2020, Fischell et al.

\* cited by examiner

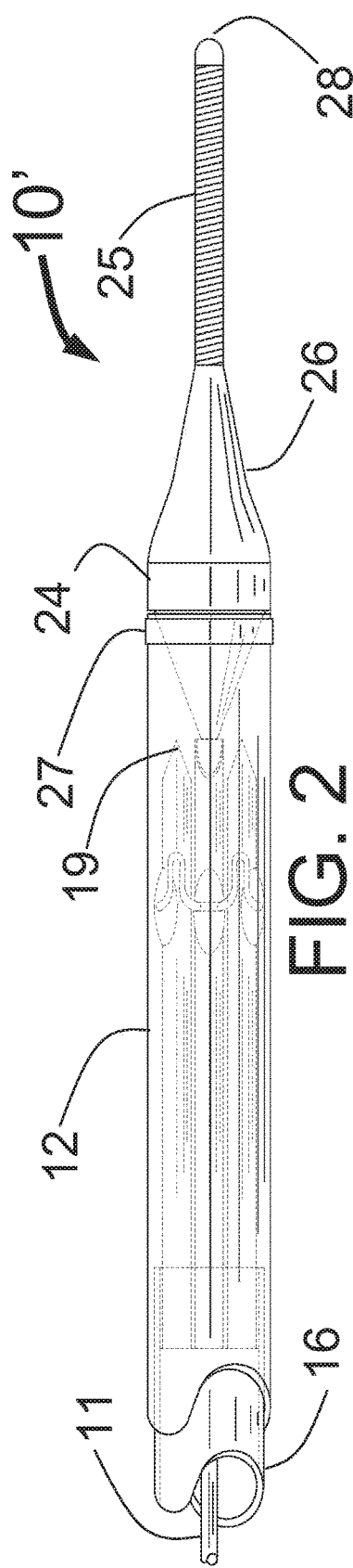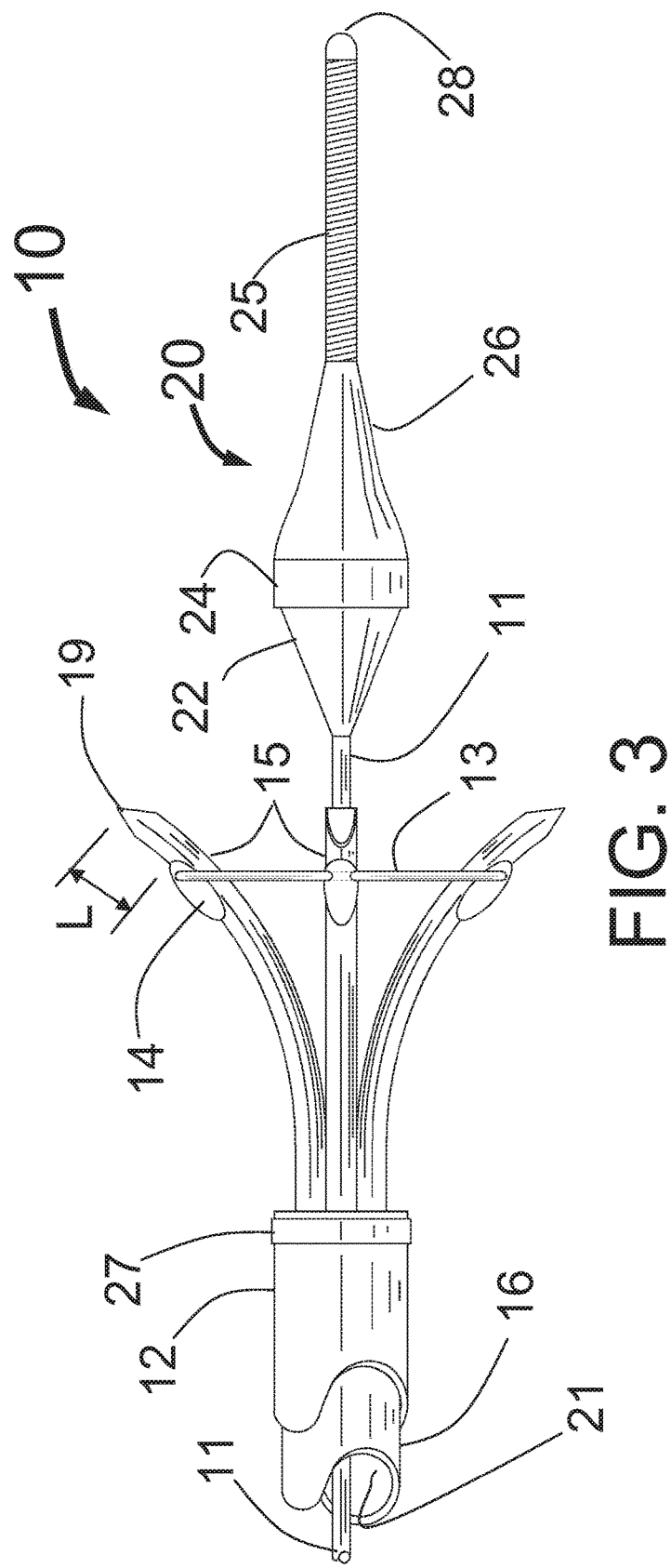
FIG. 2
FIG. 3

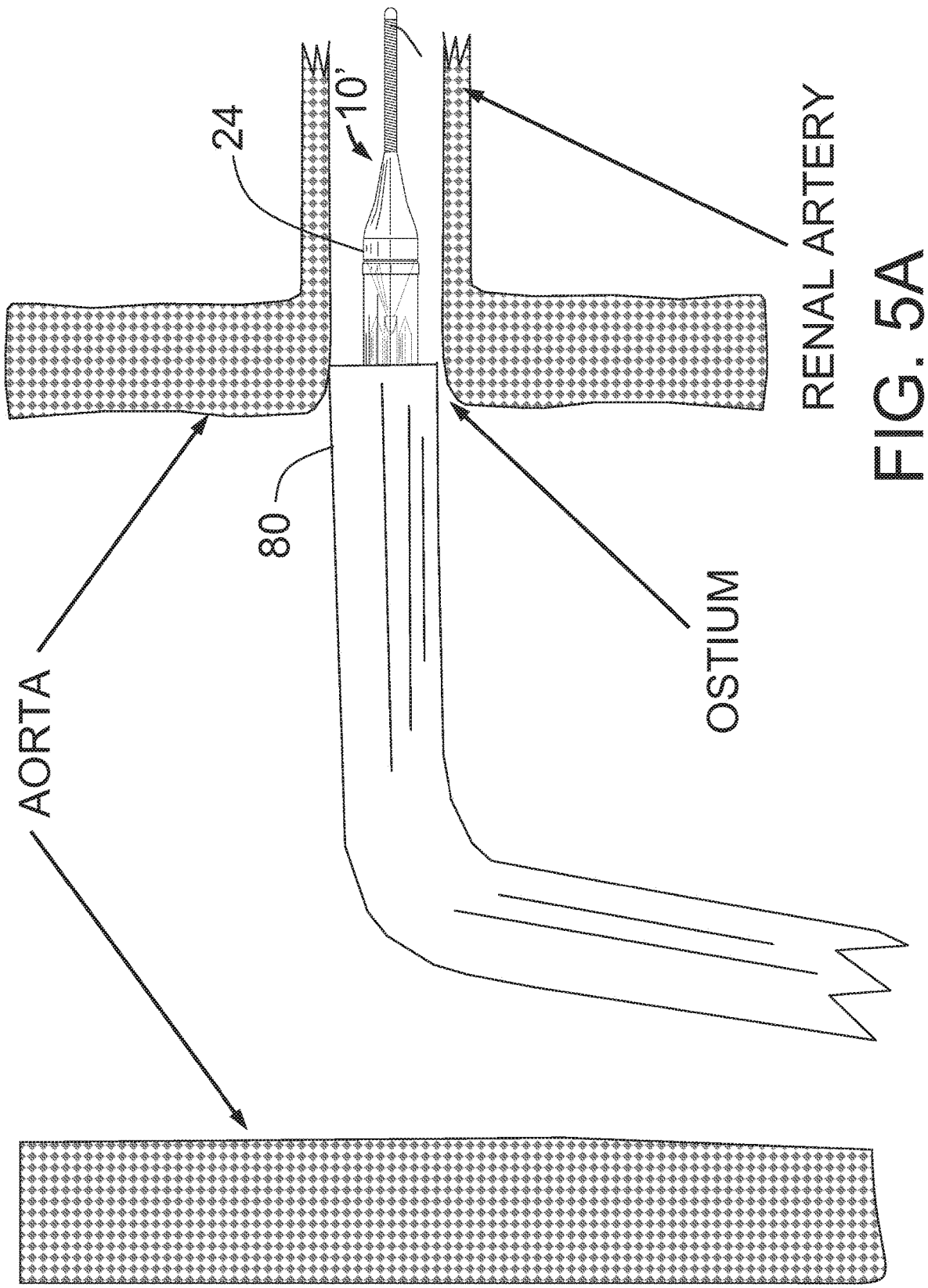

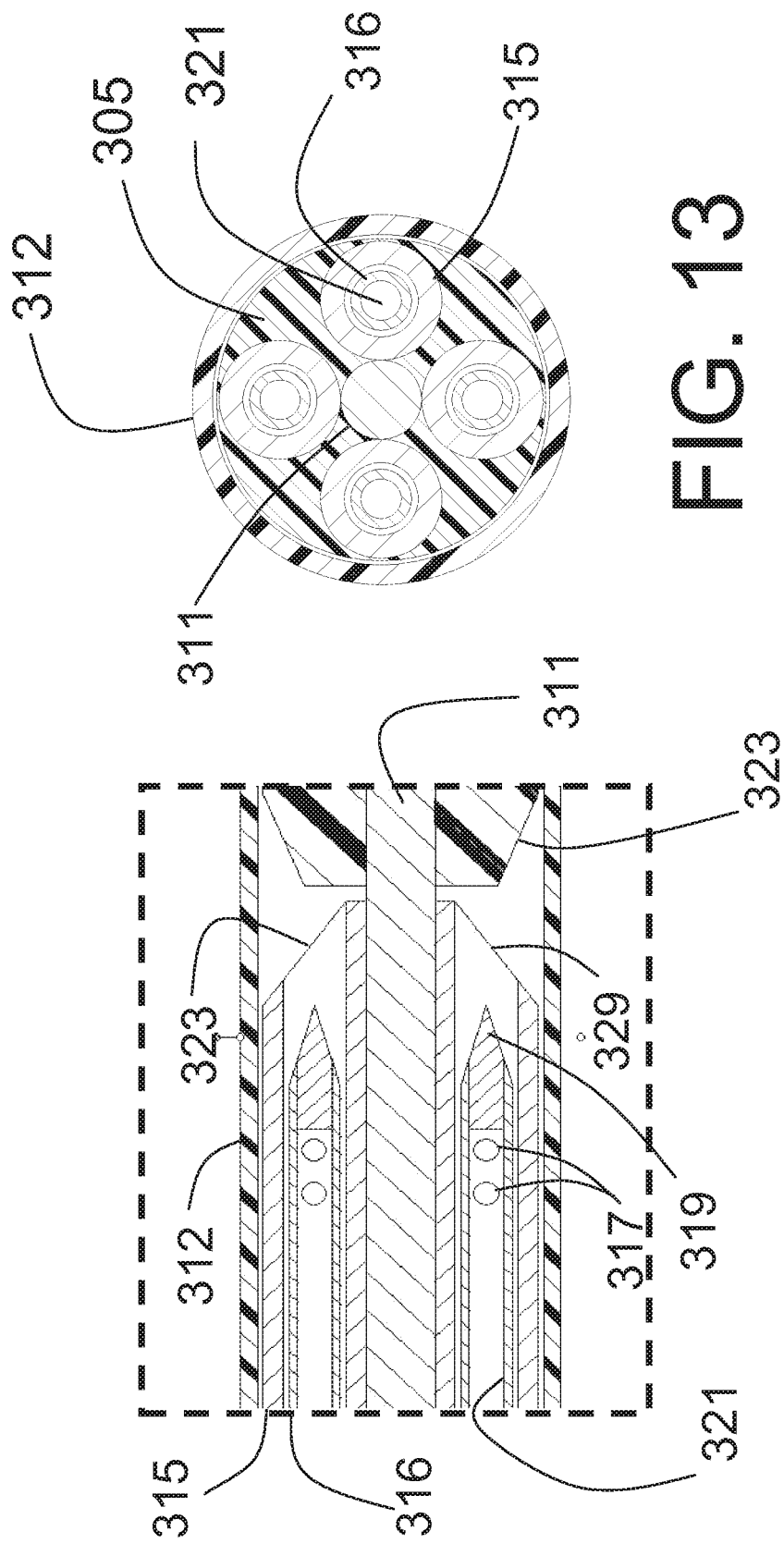

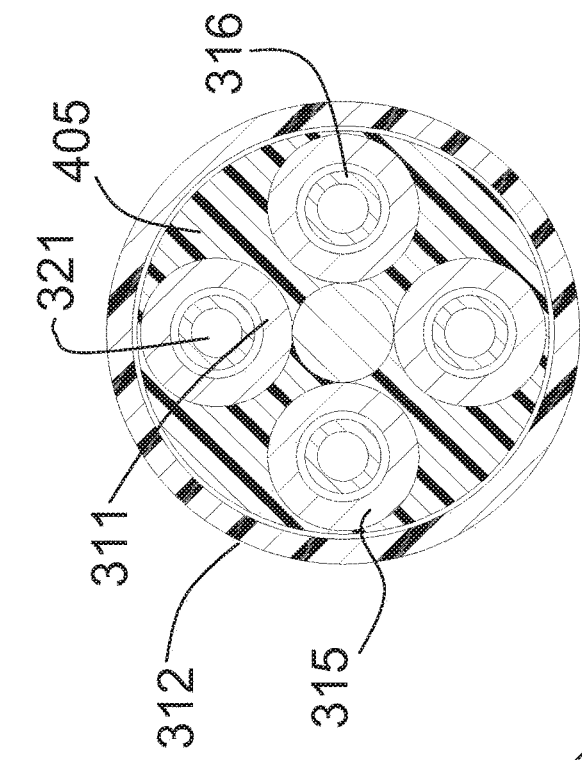
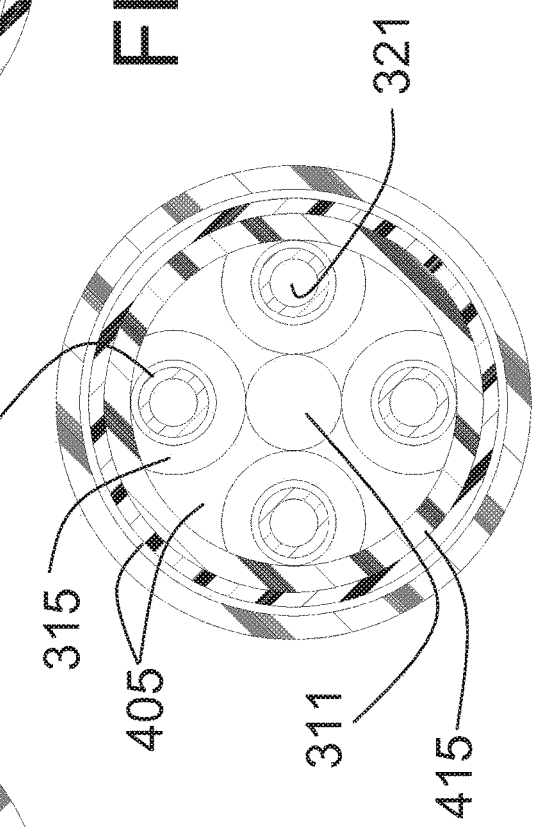
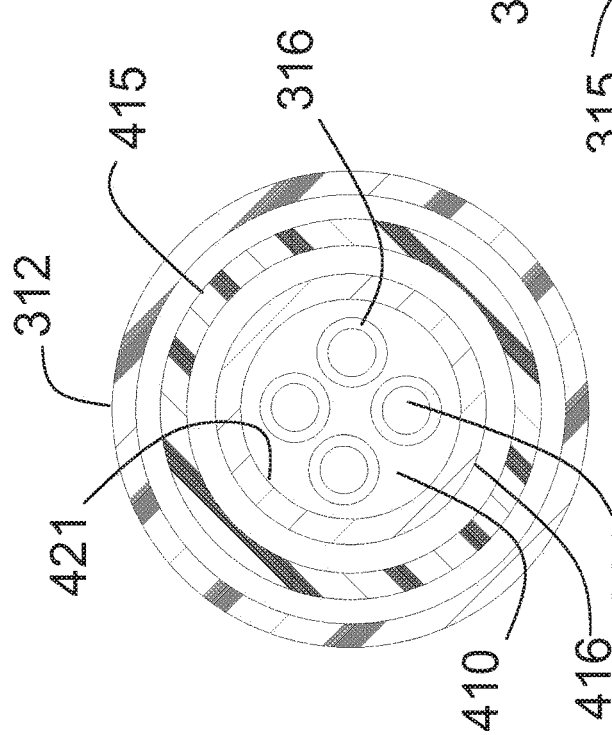
FIG. 23
FIG. 22
FIG. 21

US 11,007,329 B2

EXPANDABLE CATHETER SYSTEM FOR FLUID INJECTION INTO AND DEEP TO THE WALL OF A BLOOD VESSEL

This application is a Continuation of patent application Ser. No. 14/738,776, filed 12 Jun. 2015, now U.S. Pat. No. 10,118,004, which is a Continuation of patent application Ser. No. 13/342,521, filed January 2012, now U.S. Pat. No. 9,056,185, which is a Continuation-in-Part of patent application Ser. No. 13/216,495, filed 24 Aug. 2011, now U.S. Pat. No. 9,278,196, and a Continuation-in-Part of patent application Ser. No. 13/294,439 filed 11 Nov. 2011.

All of the foregoing priority applications are hereby incorporated by reference in their entireties.

FIELD OF USE

This invention is in the field of devices to ablate muscle cells and nerve fibers for the treatment of cardiac arrhythmias, hypertension, congestive heart failure and other disorders.

BACKGROUND OF THE INVENTION

Since the 1930s it has been known that injury or ablation of the sympathetic nerves in or near the outer layers of the renal arteries can dramatically reduce high blood pressure. At the present time, physicians often treat patients with atrial fibrillation (AF) using radiofrequency (RF) catheter systems to ablate conducting tissue in the wall of the left atrium of the heart around the ostium of the pulmonary veins. Similar technology, using radiofrequency energy, has been successfully used inside the renal arteries to ablate sympathetic and other nerve fibers that run in the outer wall of the renal arteries, in order to treat high blood pressure. In both cases these are elaborate and expensive catheter systems that can cause thermal, cryoablative, or other methods to injure surrounding tissue. Many of these systems also require significant capital outlays for the reusable equipment that lies outside of the body, including RF generation systems and the fluid handling systems for cryoablative catheters.

Because of the similarities of anatomy, for the purposes of this disclosure, the term target wall will refer here to either the wall of the left atrium surrounding a pulmonary vein or the wall of a pulmonary vein near its ostium for AF ablation applications or the wall of the aorta around the ostium of the renal artery, or within the renal artery itself, for hypertension or congestive heart failure (CHF) applications.

In the case of atrial fibrillation ablation, the ablation of tissue surrounding multiple pulmonary veins can be technically challenging and very time consuming. This is particularly so if one uses RF catheters that can only ablate one focus at a time. There is also a failure rate using these types of catheters for atrial fibrillation ablation. The failures of the current approaches are related to the challenges in creating reproducible circumferential ablation of tissue around the ostium (peri-ostial) of a pulmonary vein. There are also significant safety issues with current technologies related to very long fluoroscopy and procedure times that lead to high levels of radiation exposure to both the patient and the operator, and may increase stroke risk in atrial fibrillation ablation.

There are also potential risks using the current technologies for RF ablation to create sympathetic nerve denervation from inside the renal artery for the treatment of hypertension or congestive heart failure. The short-term complications and the long-term sequelae of applying RF energy from inside the renal artery to the wall of the artery are not well defined. This type of energy applied within the renal artery, and with transmural renal artery injury, may lead to late restenosis, thrombosis, renal artery spasm, embolization of debris into the renal parenchyma, or other problems inside the renal artery. There may also be uneven or incomplete sympathetic nerve ablation, particularly if there are anatomic anomalies, or atherosclerotic or fibrotic disease inside the renal artery, such that there is non-homogeneous delivery of RF energy This could lead to treatment failures, or the need for additional and dangerous levels of RF energy to ablate the nerves that run along the adventitial plane of the renal artery.

The currently used system for RF energy delivery also does not allow for efficient circumferential ablation of the renal sympathetic nerve fibers. If circumferential RF energy were applied in a ring segment from within the renal artery (energy applied at intimal surface to kill nerves in the outer adventitial layer) this could lead to even higher risks of renal artery stenosis from the circumferential and transmural thermal injury to the intima, media and adventitia. Finally, the "burning" or the inside of the renal artery using RF ablation can be extremely painful. Thus, there are numerous and substantial limitations of the current approach using RF-based renal sympathetic denervation.

The Bullfrog® micro infusion catheter described by Seward et al in U.S. Pat. Nos. 6,547,803 and 7,666,163 which uses an inflatable elastic balloon to expand a single needle against the wall of a blood vessel could be used for the injection of an chemical ablative solution such as alcohol but it would require multiple applications as it does not describe or anticipate the circumferential delivery of an ablative substance around the entire circumference of the vessel. The most number of needles shown by Seward is two and the two needle version of the Bullfrog® would be hard to miniaturize to fit through a small guiding catheter to be used in a renal artery. If only one needle is used, controlled and accurate rotation of any device at the end of a catheter is difficult at best and could be risky if the subsequent injections are not evenly spaced. This device also does not allow for a precise, controlled, and adjustable depth of delivery of a neuroablative agent. Another limitation of the Bullfrog® is that inflation of a balloon within the renal artery can induce stenosis due to balloon injury of the intima and media of the artery, as well as causing endothelial cell denudation.

Jacobson and Davis in U.S. Pat. No. 6,302,870 describe a catheter for medication injection into the inside wall of a blood vessel. While Jacobson includes the concept of multiple needles expanding outward, each with a hilt to limit penetration of the needle into the wall of the vessel, his design depends on rotation of the tube having the needle at its distal end to allow it to get into an outward curving shape. The hilt design shown of a small disk attached a short distance proximal to the needle distal end has a fixed diameter which will increase the total diameter of the device by at least twice the diameter of the hilt so that if the hilt is large enough in diameter to stop penetration of the needle, it will significantly add to the diameter of the device. For either the renal denervation or atrial fibrillation application, the length of the needed catheter would make control of such rotation difficult. In addition, the hilts which limit penetration are a fixed distance from the distal end of the needles. There is no built in adjustment on penetration depth which may be important if one wishes to selectively target a specific layer in the blood vessel or if one needs to penetrate all the way through to the volume past the adventitia in vessels with different wall thicknesses. Jacobson also does not envision use of the injection catheter for denervation. Finally, Jacobson in FIG. 3 when he shows a sheath over expandable needles, there is no guide wire and the sheath has an open distal end which makes advancement through the vascular system more difficult. Also the needles if they were withdrawn completely inside of the sheath they could because of the hilts, get stuck inside the sheath and be difficult to push out.

The prior art also does not envision use of anesthetic agents such as lydocaine which if injected first or in or together with an ablative solution can reduce or eliminate any pain associated with the denervation procedure.

Finally, while injection of ethanol as an ablative substance is well known and used within the heart and other parts of the body, there has been no development of an ethanol (or other liquid nerve ablation substances) injection system specifically designed for the circumferential ablation of sympathetic nerve fibers around the renal arteries.

SUMMARY OF THE INVENTION

The present invention, Intravascular Nerve Ablation System (INAS), is capable of applying an ablative fluid to produce circumferential damage in the nerve tissue that is in or near the wall of a blood vessel with a relatively short treatment time using a disposable catheter and requiring no additional capital equipment. The primary focus of use of INAS is in the treatment of cardiac arrhythmias, hypertension and congestive heart failure. Unlike the Bullfrog® or RF ablation devices that work with one or, at most two points of ablation, the present invention is designed to provide a more uniform circumferential injury to the nerves, while minimizing injury to the intima and medial layers of the vessel wall. The term circumferential delivery is defined here as at least three points of simultaneous injection of a suitable ablative solution within or just outside of a vessel wall, with the goal to ablate nerves completely around the circumference of a blood vessel. Circumferential delivery may be in a true circle or in a helical pattern so long as the entire 360 degrees or more is covered. Unlike the Jacobson device of U.S. Pat. No. 6,302,870, which does describe circumferential delivery, the present invention does not depend upon rotation of a tube to create outward movement nor does it have a fixed diameter hilt to limit penetration.

Specifically, there is a definite need for such a catheter system that is capable of highly efficient, and reproducible ablation of the nerves surrounding the renal artery ostium, or distal to the ostium in the renal artery wall, in order to damage the sympathetic nerve fibers that track from the peri-ostial aortic wall into the renal arteries, and thus improve the control and treatment of hypertension, etc.

This type of system may also have major advantages over other current technologies by allowing highly efficient, and reproducible circumferential ablation of the muscle fibers and conductive tissue in the left atrium, surrounding the ostium of the pulmonary veins or in the wall of the pulmonary veins near or at their ostium into the left atrium of the heart. Such ablation could interrupt atrial fibrillation (AF) and other cardiac arrhythmias. Other potential applications of this approach may evolve.

The present invention is a small (<2 mm diameter) catheter, which includes multiple expandable injector tubes, or guide tubes to allow passage of coaxial injector tubes, arranged circumferentially around the body of the INAS near its distal end. Each injector tube includes a needle at its distal end. Ablative fluid could be injected through the distal end of this needle which has injection egress through its distal end or through side holes placed just proximal to its distal end, needle has a (solid tipped) cutting distal end. There is a penetration limiting member as part of the INAS so that the needles will only penetrate into the tissue of the wall of the target blood vessel to a preset distance. These may be a preset distance proximal to the distal end of each needle similar to the hilts of the Jacobson et al patent or the penetration limiting member may be built into the proximal section of the INAS. Limiting penetration is important to reduce the likelihood of perforation of the vessel wall, optimize the depth of injection or to adjust the depth to be into the volume just outside of the blood vessel wall. In a preferred embodiment for renal sympathetic nerve ablation, self-expanding guiding tubes are first deployed against the inside wall of the renal artery and act as a guide for separate coaxially longitudinally moveable injector tubes with sharpened needles with injection egress port(s) near the distal end.

The penetration limiting function of the present invention INAS as described herein uses one of the following techniques that will greatly reduce the diameter of the device as compared with the Jacobson designs of U.S. Pat. No. 6,302,870 and thus also improve the ability to deliver it into a vessel of a human body such as the renal artery. These techniques include:

Use of a cord or wire attached to the multiple needles that can fold during insertion to limit the diameter of the distal section of the INAS, Use of one, two or more short NITINOL wires attached in the longitudinal direction at their proximal ends to the sides of the needle. The wires being designed to have their distal ends not be attached and having a memory state that curves away from the needle so as to act as a penetration limiting member for the needle. Such wires would fold tight against the needles to reduce the diameter of the distal section of the INAS, Use of two bends in the needle the bend forming the penetration limiting member and the bend also being in the circumferential direction so as to not increase the diameter of the distal section of the INAS, and Use of guide tubes that curve outward through which the needles slide in the longitudinal direction. The limit for penetration in this design is integral into the handles at the proximal end of the INAS and do not require diametric volume in the distal section of the INAS. This last embodiment has the added advantage of allowing adjustment of the penetration depth.

The injector tubes with distal needles are in fluid communication with an injection lumen in the catheter body, which is in fluid communication with an injection port at the proximal end of the INAS. Such an injection port would typically include a standard connector such as a Luer connector used to connect to a source of ablative fluid.

This injection system also anticipates the use of very small gauge needles (smaller than 25 gauge) to penetrate the arterial wall, such that the needle penetration could be safe, even if targeted to a plane or volume of tissue that is at, or deep to (beyond) the adventitial layer of the aorta, a pulmonary vein or renal artery. It is also anticipated that the distal needle could be a cutting needle rather than a coring needle and that the injection egress ports could be small injection holes (pores) cut into the sides of the injector tubes or distal needle, proximal to the cutting needle tip.

The expandable injector tubes or guide tubes may be self-expanding made of a springy material, a memory metal such as NITINOL or they may be made of a metal or plastic and expandable by other mechanical means. For example, the expandable legs with distal injection needles could be mounted to the outside of an expandable balloon whose diameter is controllable by the pressure used to inflate the balloon. There should be at least 2 injector tubes but 3 to 8 tubes may be more appropriate, depending on the diameter of the vessel to be treated. For example, in a 5 mm diameter renal artery, only 3 or 4 needles may be needed while in an 8 mm diameter renal one might need 6 needles.

The entire INAS is designed to include a fixed distal guide wire or be advanced over a guide wire in either an over-the-wire configuration where the guide wire lumen runs the entire length of the INAS or a rapid exchange configuration where the guide wire exits the catheter body at least 10 cm distal to the proximal end of the INAS and runs outside of the catheter shaft for its proximal section. The fixed wire version is preferred as it would have the smallest distal diameter.

The INAS would also include a tubular, thin-walled sheath that constrains the self-expanding injection tubes with distal needles and/or guiding tubes prior to deployment, and for removal from the body. The sheath also allows the distal end of the INAS to be inserted into the proximal end of a guiding catheter or introducer sheath. The sheath also serves to protect the operator(s) from possible needle sticks and exposure to blood borne pathogens at the end of the procedure when the INAS is removed from the patient's body.

It is also envisioned that the injection needles, guiding tubes and injection tubes could be formed from a radiopaque material such as tantalum or tungsten or coated, or marked with a radiopaque material such as gold or platinum so as to make them clearly visible using fluoroscopy.

It is also envisioned that one or more of the injector needles could be electrically connected to the proximal end of the INAS so as to also act as a diagnostic electrode(s) for evaluation of the electrical activity in the area of the vessel wall.

It is also envisioned that one could attach 2 or more of the expandable legs to an electrical or RF source to deliver electric current or RF energy around the circumference of a target vessel to the ostial wall to perform tissue and/or nerve ablation.

It is also envisioned that this device could utilize one, or more than one neuroablative substances to be injected simultaneously, or in a sequence of injections, in order to optimize permanent sympathetic nerve disruption in a segment of the renal artery (neurotmesis). The anticipated neurotoxic agents that could be utilized includes but is not limited to ethanol, phenol, glycerol, local anesthetics in relatively high concentration (e.g., lidocaine, or other agents such as bupivicaine, tetracaine, benzocaine, etc.), anti-arrhythmic drugs that have neurotoxicity, botulinum toxin, guanethidine, heated fluids including heated saline, hypertonic saline, KCl or heated neuroablative substances such as those listed above.

The present invention also envisions use of anesthetic agents such as lydocaine which if injected first or in or together with an ablative solution can reduce or eliminate any pain associated with the denervation procedure.

The present invention also envisions use of a buffer before, after and/or between injections of contrast, anesthetic agents and/or neuroablative substances. For example, saline solution should be injected after the neuroablative substance for the first renal artery treated to make sure that all the neuroablative substance has been delivered and there is only saline in the injection lumen(s) and dead space of the INAS. Thus when the procedure begins on the second renal artery, contrast or an anesthetic agent can be delivered first to the desired location rather than having any residual ablative substance that is left in the INAS come out first. Ideally, once could envision the following sequence for injection using the INAS to ablate the sympathetic nerves in both renal arteries.

1. Flush the INAS out of the body with saline solution
2. Place the INAS and inject contrast to ensure that the injection egress points are properly located
3. Inject an anesthetic agent to prevent pain during ablation
4. Inject the neuroablative substance
5. Inject sufficient saline solution to flush all of the neuroablative substance from the INAS
6. Close the INAS and retract the INAS back into the guiding catheter,
7. Access the other renal artery
8. Place the INAS and inject contrast to ensure that the injection egress points are properly located
9. Inject an anesthetic agent to prevent pain during ablation
10. Inject the neuroablative substance
11. Inject sufficient saline solution to flush all of the neuroablative substance from the INAS
12. Close the INAS and retract the INAS back into the guiding catheter,
13. Remove the INAS from the body It is also envisioned that saline can be injected between steps 2 and 3, 3 and 4, 8 and 9 and/or 9 and 10.

It is also envisioned that one could utilize imaging techniques such as multislice CT scan, MRI or intravascular ultrasound imaging to get an exact measurement of the thickness and anatomy of the target vessel wall (e.g., renal artery) such that one could know and set the exact and correct penetration depth for the injection of the ablative agent prior to the advancement of the injector needles or injector tubes. The use of IMUS prior to use of the INAS may be particularly useful in order to target the exact depth intended for injection. This exact depth can then be targeted using the adjustable depth of penetration feature in our preferred embodiment(s). The selection of penetration depth can be accomplished using the proximal handles of the guide tube embodiment or by selection of an appropriate product code for the other designs that might have two to five versions each with a different penetration depth limit.

For use in the treatment of hypertension or CHF, via renal sympathetic nerve ablation, the present preferred embodiment of this invention INAS would be used with the following steps:

1. Engage a first renal artery with a guiding catheter placed through the femoral artery.
2. Advance the distal end of the INAS with a fixed distal guidewire into, and advance the INAS through the guiding catheter, until the distal end of the guiding tubes are passed beyond the distal end of the guiding catheter and into the renal artery.
3. Pull back the sheath allowing the expandable guide tubes to open up until the distal ends of the guide tubes press outward against the inside wall of the renal artery.
4. With the injector guide tubes having an outward curve or angle, the guide tube handle that controls the longitudinal motion of the guide tubes is then moved in the distal direction allowing the distal ends of the guide tubes that are touching the inside wall of the renal artery to further press against the intima and begin to flex backwards.

5. The guide tubes will then have their open distal ends facing into the renal artery wall. At this point contrast injection from the guiding catheter can confirm the correct spacing and position of the guide tubes.
6. Next, the injection tubes are be advanced coaxially through the guide tubes to an adjustable distance with a target of placing the injection egress to be at or just deep to the adventitial plane of the renal; artery. One or more penetrating limiting member(s) will allow the needles only to penetrate a preset distance (typically between 0.5 to 3 mm but preferably about 2-3 mm) into the vessel wall of the renal artery. Ideally, the very small gauge injection needles may be advanced to ~2-3 mm depth in the renal artery to deliver the neuroablative agent(s) at or deep to the adventitial plane, in order to minimize intimal and medial renal artery injury. The correct depth can be determined prior to the INAS treatment using CT scan, MRI or intravascular ultrasound to measure the renal artery wall thickness, such that the correct initial depth setting for the injector tube penetration is known prior to advancing the needles.
7. Attach an injection system, syringe or multiple syringes through a manifold to the connector at the INAS proximal end used to supply the ablative fluid. An anesthetic agent such as lidocaine can then be injected to eliminate or reduce any pain associated with the denervation procedure. The anesthetic agent can be injected before, after or at the same time as a small volume of contrast would be injected through the system, exiting at the injection egress near the distal end of the injector tubes to confirm the correct depth for injection of the neuroablative agent. Adjustment of the depth is possible at this time if the injection plane is determined to be to shallow (e.g., in media) or too deep (well outside the adventitial plane).
8. Inject an appropriate volume of ethanol (ethyl alcohol), phenol, glycerol, lidocaine, bupivacaine, tetracaine, benzocaine, guanethidine, botulinum toxin or other appropriate neurotoxic fluid, including a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid from the syringe or injection system through the catheter and out of the needles into the vessel wall and/or the volume just outside of the vessel. A typical injection would be 1-10 ml. This should produce a multiplicity of ablation zones (one for each injector tube) that will intersect to form an ablative ring around the circumference of the target vessel. Contrast could be added to the injection either during a test injection or during the therapeutic injection to allow x-ray visualization of the ablation zone.
9. Once the injection is complete, retract the INAS injector tubes back inside the guide tubes. Then, retract and re-sheath the guide tubes by advancing the sheath over the guide tubes. This will collapse the guide tubes back under the sheath. The entire INAS can then be pulled back into the guiding catheter.
10. In some cases, one may rotate the INAS 20-90 degrees and then repeat the injection if needed to make an even more definitive ring of ablation.
11. The same methods as per prior steps can be repeated to ablate tissue in the contralateral renal artery.
12. Remove the INAS from the guiding catheter completely.
13. Remove all remaining apparatus from the body.
14. A similar approach can be used with the INAS, via transeptal access into the left atrium to treat AF, via ablation of tissue in the vessel wall of one or more pulmonary veins. When indicated, advance appropriate diagnostic electrophysiology catheters to confirm that the ablation (in the case of atrial fibrillation) has been successful It is also envisioned that one could mount injector tubes with needles on the outer surface of an expandable balloon on the INAS in order to deliver 2 or more needles into the vessel wall of a target vessel to inject ablative fluid.

Although the main embodiment of this invention utilizes two or more needle injection sites to circumferentially administer alcohol or other neuro-toxic fluid(s) to the wall of the renal artery for sympathetic nerve ablation, it is also envisioned that other modifications of this concept could also be utilized to achieve the same result. In one case it is envisioned that circumferential fluid based (ethanol or other ablative fluid, a combination of ablative fluids, or heated fluid) could be administered in a circumferential fashion to a "ring segment" of the renal artery by injecting the ablative fluid into a space between two inflated balloons. Thus, after inflating a proximal occlusive balloon and a distal occlusive balloon, the ablative fluid would be injected into the space between the two balloons and allowed to dwell for a short period of time allowing the fluid, such as ethanol to penetrate through the arterial wall and reach the adventitial layer, thus disrupting and ablating the sympathetic nerves running in this space. After the dwell period the space could be flushed with saline and the balloons deflated.

Similarly, a single balloon with a smaller diameter near the middle of the balloon could function in the same way, as the ethanol or other ablative fluid, or a combination of ablative fluids, or heated fluid is injected in the "saddle-like" space in the central part of the balloon that is not touching the arterial wall.

It is also envisioned that another embodiment may include a circumferential band of polymer, hydrogel or other carrier, on the central portion of an inflatable balloon with the carrier containing the neurotoxic agent(s), such as alcohol, phenol, glycerol, lidocaine, bupivacaine, tetracaine, benzocaine, guanethidine, botulinum toxin, etc. The balloon would be inflated at relatively low pressure to oppose the intimal surface of the renal arterial wall, and inflated for a dwell time to allow penetration of the neurotoxic agent, circumferentially, into a "ring segment" of the renal artery and allow ablation of the sympathetic nerve fibers running near or in the adventitial plane.

It is also envisioned that the INAS catheter could be connected to a heated fluid, or steam, source to deliver high temperature fluids to ablate or injure the target tissue or nerves. The heated fluid could be normal saline, hypertonic saline, alcohol, phenol, lidocaine, or some other combination of fluids. Steam injection, of saline, hypertonic saline, ethanol, or distilled water or other fluids via the needles could also be performed in order to achieve thermal ablation of target tissue or nerves at and around the needle injection sites.

It is also envisioned that the INAS could utilize very small diameter needle injection tubes (e.g., 25-35 gauge) with sharpened needles at their distal ends such that the needles would be advanced to, or even through the adventitial plane of the renal artery or aortic wall using a penetration limiting member(s) or the combination of the guide tubes with an adjustable depth advancement of injector tubes through the guide tubes in order to set the depth of penetration, and allow one to "bathe" the adventitial layer containing the sympathetic nerves with neurotoxic fluid, while causing minimal injury to the intimal and medial vessel wall layers, These very tiny needles could pass transmurally through the arterial wall yet create such tiny holes in the arterial wall that blood leakage from the lumen to outside the vessel as well as medial layer injury would be minimal, and thus safe. Thus, the present invention could have the injection be either into the wall of the renal artery, into the adventitia of the renal artery or deep to the adventitial layer of the renal artery such that the injection needles or egress from injection tubes would occur via penetration all the way through the arterial wall to allow the ablative fluid to flow around and "bathe" the outside of the artery with one or more neuroablative substances.

Another embodiment may include two or more pores, or small metallic (very short) needle like projections on the outer surface of the central portion of an inflatable balloon, that would be in fluid communication with an injection lumen to allow injection into the wall of the renal artery and allow circumferential delivery of a neurotoxic agent(s). Given these teachings and embodiment descriptions, other similar techniques could be envisioned to allow other variations upon this concept of a balloon expandable, circumferential ablation system for renal artery sympathetic nerve ablation.

Another embodiment of the present invention, as described in the methods above, places the means to limit penetration of the vessel wall at the proximal end of the INAS. In this embodiment, at least three guide tubes with expandable distal portions run along the distal portion of the length of the INAS. A guide tube handle with optional flushing port is attached to the proximal end of the INAS and controls the longitudinal motion of the guide tubes.

One injection tube is included for each guide tube where the injection tubes have sharpened (cutting needle) distal ends with injection egress ports just proximal to the cutting needle tip. The injection tubes are located coaxially inside of the guide tubes. The distal ends of the sharpened injection needles at the distal ends of the injection tubes are initially "parked" just proximal to the distal end of the guide tubes. A proximal injection tube handle attached to the proximal end of the injection tubes, or to the proximal end of a single injector tube that connects to the multiple injector tubes, is separated at its distal end from the proximal end of the guide tube handle forming a needle advancement gap. The injector tube handle has means to adjust the needle advancement gap distance. Alternately, the adjustment could be on the guide tube handle or a separate mechanism between the injector tube handle and guide tube handle. A fitting for injection of an ablative fluid is attached to the injector tube handle and is in fluid communication with the injection lumens of the injector tubes.

In its initial configuration a sheath lies outside of the guide tubes constraining them. The proximal end of the sheath is attached to a sheath handle which can be locked down to prevent longitudinal motion with respect to the guide tubes or unlocked to allow the sheath to be moved in the proximal or distal direction to open and close the INAS.

The process to use the INAS handles is to have each of the lumens in the INAS flushed with normal saline. The distal end of the INAS is then advanced through a guiding catheter into a vessel such as a renal artery. The sheath control handle is then pulled back holding the guide tube handle in position. This will allow the distal portion of the guide tubes to expand outwardly against the wall of a vessel such as a renal artery. Optionally, after the sheath is pulled back, the guide tubes can then be pushed slightly forward using the guide tube handle to ensure they are engaged firmly against the vessel wall. The injector tube handle is then advanced so as to push the distal ends of the injection tubes having sharpened injection needles out of the distal end of the guide tubes which are touching the inside of the vessel wall. The needles will penetrate into the media of the vessel wall. Depending on the advancement gap, the penetration of the needles into the vessel wall can be limited. This can permit selective injection through the injection egress ports of the needles into the media, adventitia, outside of the adventitia or any combination of these depending on the number and location of injection egress ports. After the needles are properly placed into or through the vessel wall, a source of ablative fluid such as ethanol is attached to the fitting in the injection tube handle and the fluid is injected through the lumens inside the injector tubes and out through the injection egress ports into the tissue.

After the injection is complete, the injection tube handle is pulled back to retract the needles into the distal portion of the guide tubes. The sheath control handle is then advanced to collapse the guide tubes and close the INAS. The sheath control handle is then locked down to prevent inadvertent opening of the INAS. The INAS is then pulled back onto the guiding catheter and the same procedure can be repeated for the other renal artery.

Although it is envisioned that there could be a number from one to 8 injector tubes inside of 8 guide tubes, it is likely that 3 or 4 tubes is optimal for circumferential tissue ablation.

While complete circular ablation of the sympathetic nerves around the outside of a renal artery will be very effective in reducing blood pressure, it may be desirable to longitudinally offset the injection points to create a helical (spiral) ablation pattern that will still completely ablate the sympathetic nerves in the outer layers of each renal artery while reducing the damage to the artery circumferentially at a single location. Thus an embodiment of the present invention is envisioned where each successive injection egress point is longitudinally offset from adjacent egress points.

While the examples of use of the present invention disclosed herein are focused on renal denervation, it is envisioned that the present invention fluid injection system can be used for any application where injection into the wall of a blood vessel or beyond (deep to) the wall of a blood vessel is desired. Examples include injection of a cytostatic substance such as sirolimus for preventing arterial restenosis, and injection of a chemotherapy drug into or beyond the hepatic artery for treatment of liver cancer.

Thus it is an object of the present invention INAS is to have a percutaneously delivered catheter that can be used to treat atrial fibrillation with one, or more injections of an ablative fluid into the vessel walls of the pulmonary veins near the ostium, or into the left atrial tissue surrounding one or more of the pulmonary veins.

Another object of the present invention INAS is to have a percutaneously delivered catheter that can be used to treat hypertension with one, or more injections of an ablative fluid into or deep to, the vessel wall of the renal arteries, or into the wall of the aorta surrounding the ostium of the renal artery.

Another object of the present invention INAS is to facilitate injection of an ablative fluid into or beyond the outer layers of the renal artery to reduce or prevent injury to the inner layers including the media of the renal artery.

Still another object of the present invention INAS is to have a percutaneously delivered catheter that includes a multiplicity of circumferentially expandable injector tubes, each tube having a needle at its distal end with injection egress allowing the delivery of an ablative fluid into the wall of a target vessel or into the space beyond the vessel wall.

Still another object of the invention is to have a flexible penetration limiting member or means attached just proximal to the distal end of each injector needle, or relatively blunt tipped guiding tubes to limit the depth of needle penetration into, or just through, the vessel wall.

Still another object of the present invention is to have a sheath that in conjunction with a distal tip provide for open and closed positions of the INAS. The closed position has the sheath and distal tip touching so as to totally enclose the sharpened needles while the open position allows the needles to expand outward for injection of the ablative fluid into or deep to the vessel wall.

Yet another object of the present invention is to use heated or cooled ablative fluid to be the source of the tissue ablation such as with heated or cooled normal saline or enhance the efficacy of an already ablative fluid such as ethanol.

Yet another object of the present invention INAS is to have one or more of the injector needles act as diagnostic electrodes for measurement of electrical activity within the wall of the target vessel.

Yet another object of this invention is to use a multiplicity of coaxially guided injector tubes that move slidably within corresponding expandable guiding tubes, to allow the safe, controlled and adjustable depth of passage of injector tubes with sharpened needles at their distal ends into and/or through the wall of a target vessel, to allow controlled chemoablation of nerves in the adventitial layer of an artery while minimizing intimal and medial injury of said artery.

Yet another object of the present invention is to provide injection of an anesthetic agent before or during injection of the ablative fluid so as to prevent or reduce any pain associated with the denervation procedure.

Yet another object of the present invention is to provide injection egress points that form a helical pattern which will still provide ablation of all fibers of the sympathetic nerves in the outer layers of a renal artery with less risk of circumferential damage to the artery, thus potentially reducing the risk of negative (arterial) remodeling.

These and other objects and advantages of this invention will become obvious to a person of ordinary skill in this art upon reading of the detailed description of this invention including the associated drawings.

BRIEF DESCRIPTION OF THE DRAWINGS

FIG. 2 is a schematic view of the distal portion of the INAS in its closed position as it would be configured for delivery into the human body or to cover the injector needles during removal from the human body.

FIG. 3 is a schematic view of the distal portion of the INAS in its open position as it would be configured for delivery of an ablative solution into the target vessel wall.

FIG. 5A is a schematic view of the distal portion of the closed INAS of FIG. 2 as it is first advanced out of a guiding catheter into a renal artery.

FIG. 12 is an enlargement of the area S12 of FIG. 11 showing the distal portion of the injector tubes and guide tubes.

FIG. 13 is a circumferential cross section at S13-S13 of the INAS of FIG. 11.

FIG. 21 is a circumferential cross section at S21-S21 of the INAS central transition portion of FIG. 20.

FIG. 22 is a circumferential cross section at S22-S22 of the INAS central transition portion of FIG. 20.

FIG. 23 is a circumferential cross section at S23-S23 of the INAS central transition portion of FIG. 20.

DETAILED DESCRIPTION OF THE DRAWINGS

Figure 1:
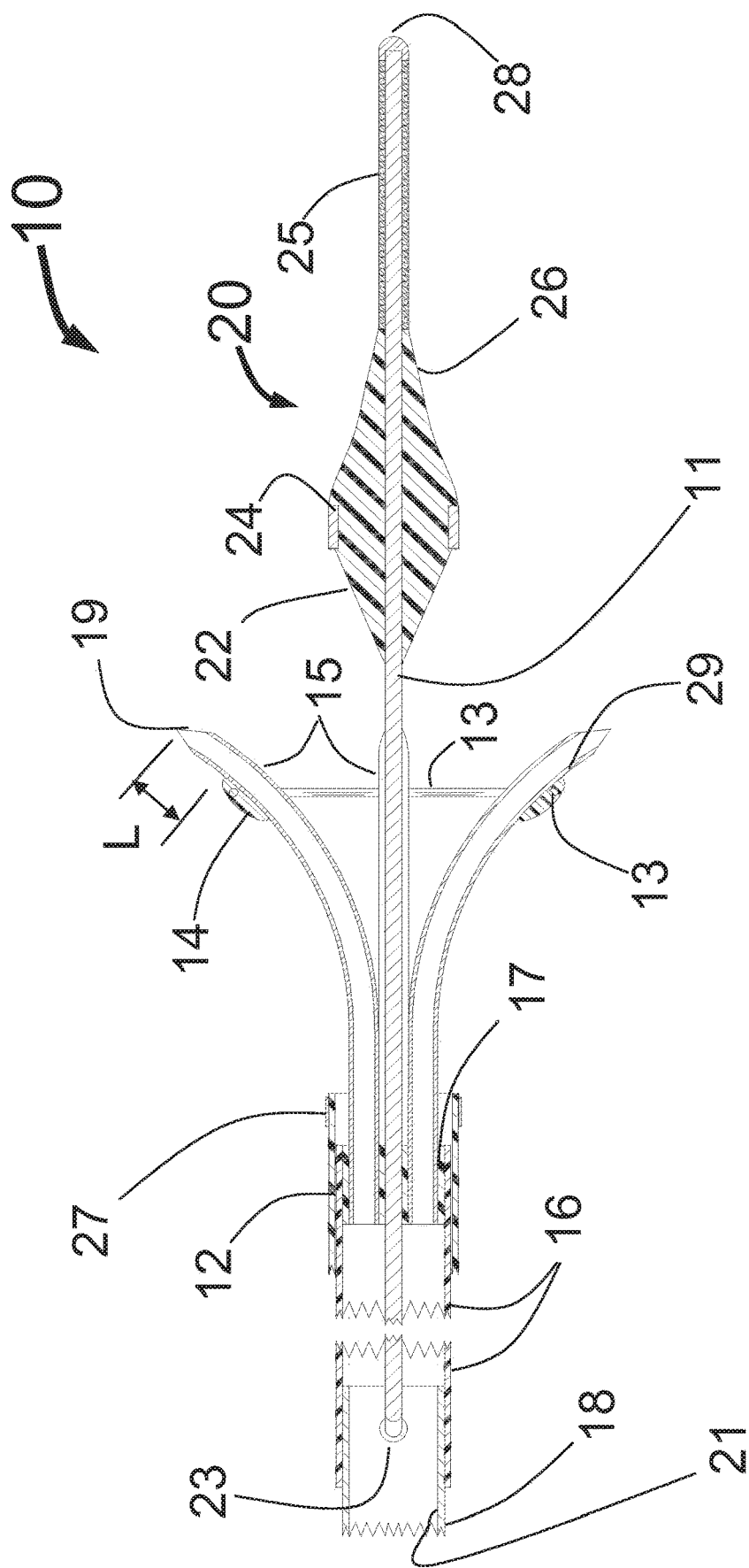
FIG. 1 is a longitudinal cross section drawing of the distal portion of the present invention Vascular Nerve Ablation System (INAS) having a fixed guide wire at its distal end.

FIG. 1 is a longitudinal cross section drawing of the distal portion of the present invention Vascular Nerve Ablation System (INAS) 10 having a fixed guide wire 25 with tip 28 at its distal end. FIG. 1 shows the INAS 10 in its fully open position with the self-expanding injector tubes 15 with distal ends sharpened to form injection needles 19 open to their maximum diameter. Flexible cords 13 with adhesive 14 that attaches the cords 13 to the injector tubes 15 act as a penetration limiting member to prevent the distal tip of the needles 19 from penetrating more than a maximum distance L into a vessel wall. The injector tubes can be made from any springy material with the preferred material being NITINOL. A separate spring or inflatable balloon could be placed inside of the injector tubes if the tubes are self-expanding to achieve the same objective. A balloon while increasing the diameter of the system would be able to push the needles with great force into the vessel wall.

A sheath 12 with radiopaque marker 27 is shown in FIG. 1 in its position where it has been pulled back to allow full expansion of the injector tubes 15. There are 4 injector tubes 15 in this embodiment of the INAS 10 although as few as 2 and as many as 12 are envisioned. The distance L can be between 0.2 and 2 mm with the optimal being about 1 mm.

The distal section 20 of the INAS 10 includes the distal wire 25, tapered flexible tip 26, radiopaque maker 24 and sheath engagement section 22 that assures that the distal portion of the INAS 10 will properly pull back into the sheath 12 following use of the INAS 10 to ablate tissue in a vessel of the human body. The INAS 10 is fully closed when the two radiopaque markers 27 and 24 are next to each other. This provides a visual indication during fluoroscopy.

The proximal end of the injector tubes 15 are held by a manifold 17 that is attached inside the distal end of the outer tube 16 and the core wire 11. The proximal end of the outer tube 16 is attached to a hypotube 18 that continues to the proximal end of the INAS 10. The hypotube 18 is typically made from a metal like 316 Stainless steel and the outer tube 16 is made from a plastic or metal reinforced plastic so that it is flexible enough to allow the INAS to easily be advanced and retracted around the bend in a typical guiding catheter such as that used for angioplasty or stenting of the renal arteries. The outer tube 16 would typically be between 5 and 30 cm long although it is also envisioned that the INAS 10 could be designed without a hypotube 18 and only a plastic or metal reinforced plastic outer tube 16 running to the proximal end.

The core wire 11 is attached to the inside of the hypotube 18 at junction point 23. This attachment could for example be by adhesive means, welding or brazing. Spot welding is the preferred method. In this way, the core wire 11 that supports the fixed wire 25 cannot be easily detached form the INAS 10. The injector lumen 21 inside of the hypotube 18 connects to the lumen of the outer tube 16 which is in fluid communication with the injector tube lumens 29 of each of the expandable tubes 15 allowing an ablative substance or solution to flow from the proximal end of the INAS 10 through the hypotube 18, through the outer tube 16, through the expandable injector tubes 15 and out of the sharpened injector needles 19 into a vessel wall.

FIG. 2 is a schematic view of the distal portion of the INAS 10' in its closed position as it would be configured for delivery into the human body or to cover the injection needles 19 during removal from the human body. The INAS 10' includes fixed wire 25 with tip 28, core wire 11, outer tube 16 and sheath 12. In this configuration the two radiopaque markers 27 and 24 are adjacent to each other with the sheath 12 being advanced to it fully distal position. Of great importance in this design is that in the closed position, the sharpened needles 19 are completely enclosed by the sheath 12 which is closed over the proximal portion of the tapered tip 26.

FIG. 3 is a schematic view of the distal portion of the present invention Intravascular Nerve Ablation System (INAS) 10 in its fully open position having a fixed guide wire 25 with tip 28 at its distal end. FIG. 3 shows the INAS 10 in its fully open position with the self-expanding injector tubes 15 with distal ends sharpened to form injection needles 19 open to their maximum diameter. Flexible cords 13 with adhesive 14 that attaches the cords 13 to the injector tubes 15 act as a penetration limiting member to prevent the distal tip of the needles 19 from penetrating more than a maximum distance L shown in FIGS. 1 and 3 into a vessel wall.

A sheath 12 with radiopaque marker 27 is shown in FIG. 3 in its position where it has been pulled back to allow full expansion of the injector tubes 15. There are 4 injector tubes 15 in this embodiment of the INAS. The distal section 20 of the INAS 10 includes the fixed distal wire 25, tapered flexible tip 26, radiopaque maker 24 and sheath engagement section 22 that assures that the distal portion will properly pull back into the sheath 12 following use of the INAS 10 to ablate tissue in a vessel of the human body. Also shown in FIG. 3 are the outer tube 16 with injection lumen 21 and core wire 11.

Figure 4:
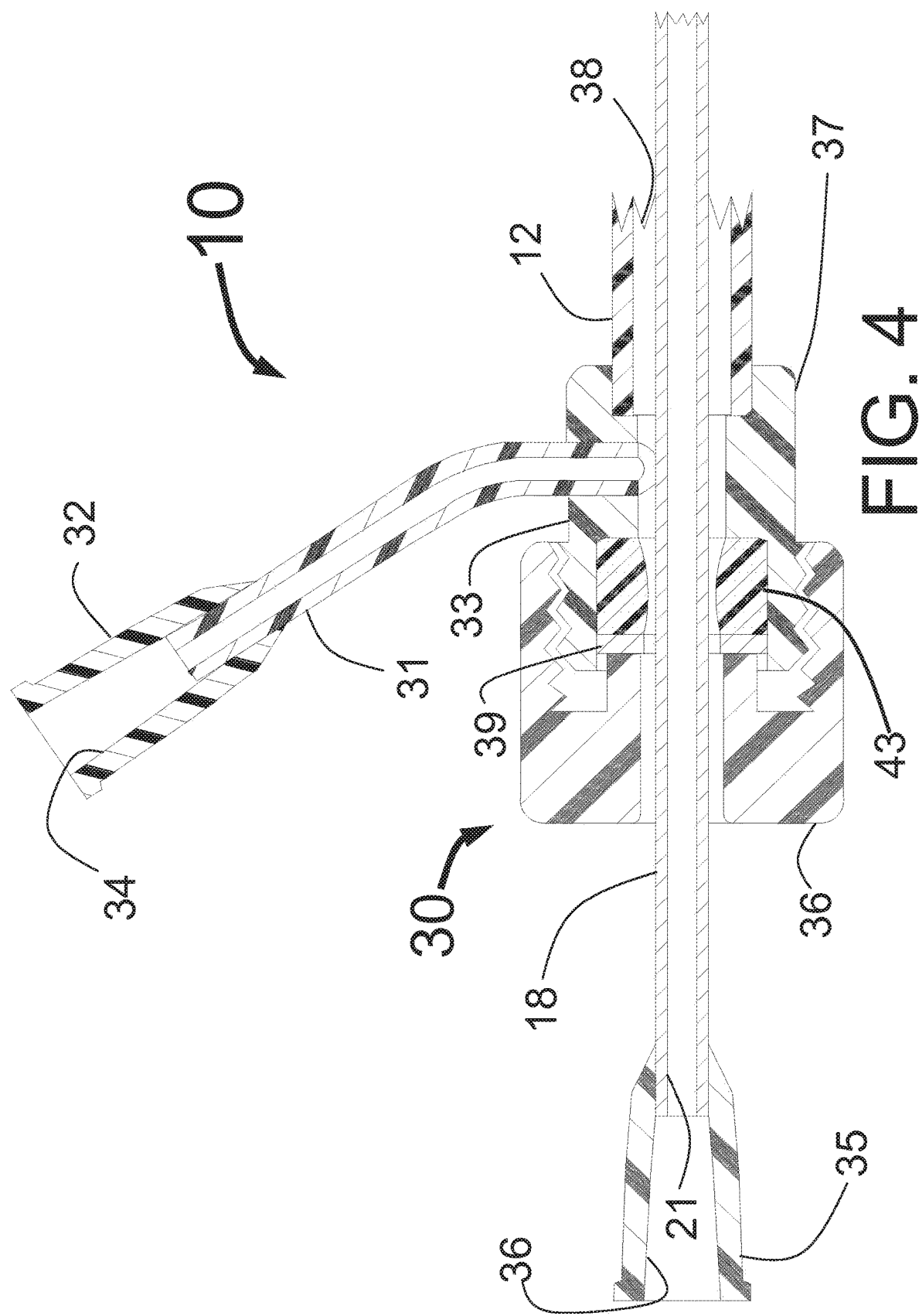
FIG. 4 is a longitudinal cross sectional drawing of the proximal end of the fixed wire embodiment of the INAS of FIGS. 1 through 3.

FIG. 4 is a longitudinal cross sectional drawing of the proximal end of the fixed wire embodiment of the INAS 10 of FIGS. 1 through 3. The hypotube 18 with injection lumen 21 also shown in FIG. 1, has a Luer fitting 35 with lumen 36 attached to its proximal end allowing a source of an ablative substance of solution to be injected through the lumen 36 of the Luer fitting 35 into the lumen 21 of the hypotube 18 and subsequently out of the injection needles 19 of FIGS. 1 through 3. The proximal end of the sheath 12 is attached to the distal end of the Tuohy-Borst fitting 30 with handle, 36, inner hub 33 washer 39 and O-Ring 43. As the handle 36 is tightened by screwing it down over the inner hub 33, the O-Ring will compress sealing the Tuohy-Borst fitting 30 against the hypotube 18. A side tube 31 with Luer fitting 32 having a lumen 34 is designed to allow the lumen 38 between the inside of the sheath 12 and hypotube 18 to be flushed with saline before insertion of the INAS 10 into a human body. Before insertion into the body, the Tuohy-Borst fitting 30 is tightened onto the hypotube 18 with the sheath 12 in its most distal position and the INAS 10' closed as is shown in FIG. 2. When in the distal end of the INAS 10' is properly positioned in one of the renal arteries, the Tuohy-Borst fitting is loosened and the handle 36 is pulled in the proximal direction while the Luer fitting 35 is held in place. This will open the INAS 10 and allow the injector tubes 15 of FIG. 1 to expand outward in the vessel.

FIG. 5A is a schematic view of the distal portion of the closed INAS 10' of FIG. 2 as it is first advanced out of a guiding catheter 80 into a renal artery just distal to the ostium with the aorta. The INAS 10' is advanced until the marker band 24 distal to the distal end of the guiding catheter 80. It is anticipated that an optimal distance of 5 to 15 mm distal would work best although shorter and longer distances are possible depending on the geometry of the renal artery and the distance of penetration of the guiding catheter 80 into the ostium of the renal artery.

Figure 5B:
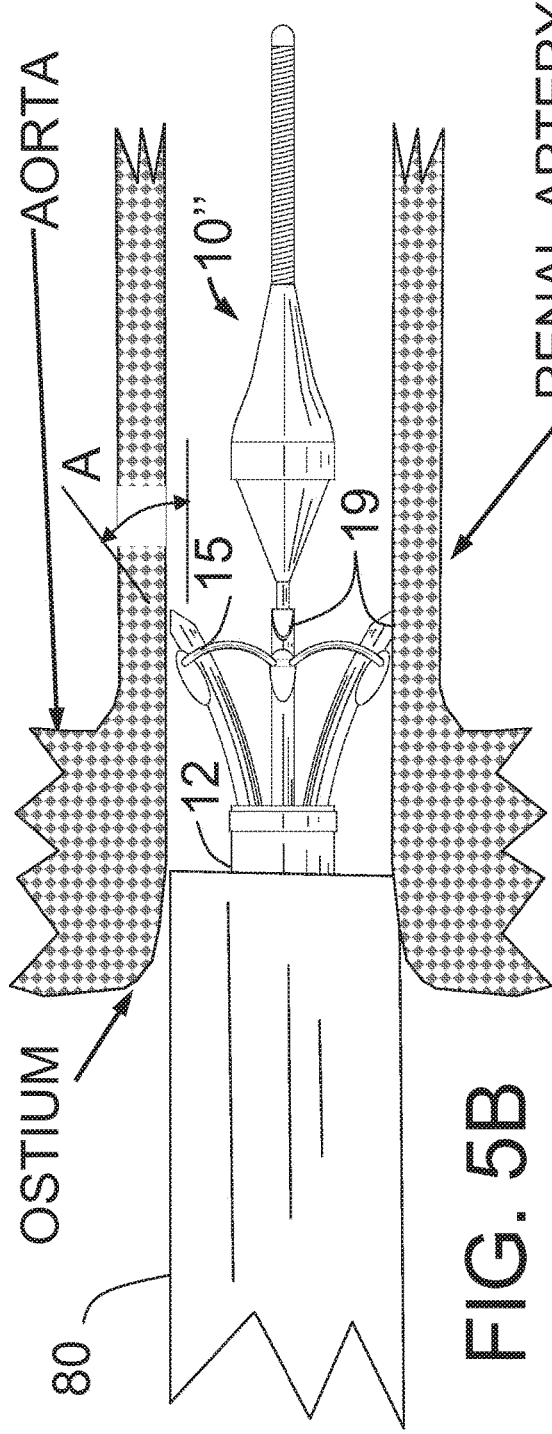
FIG. 5B is a schematic view of the distal portion of the closed INAS as the sheath is being pulled back to allow the expandable tubes open against the wall of the renal artery distal to the ostium.

FIG. 5B is a schematic view of the distal portion of the closed INAS 10" as the sheath 12 is being pulled back to allow the expandable tubes 15 open against the wall of the renal artery just distal to the ostium into the aorta. In this position, it is desired that the angle A at which the distal end of the injection needles engage the inside of the vessel wall should be less than 80 degrees and ideally between 40 and 60 degrees. If the angle is too large, the injection tubes could buckle backwards instead of pushing the sharpened needles into the vessel wall. If the angle is too small, the needles might not penetrate properly and might slide distally along the inside of the vessel wall. After the sheath 12 is pulled back so it no longer constrains the expandable injector tubes 15, the INAS 10" is then pushed in the distal direction allowing the injector tubes 15 to continue their outward expansion as the injection needles 19 penetrate into the wall of the renal artery. The penetration will stop when the cords 13 engage the wall of the renal artery limiting the penetration of the needles 19. Alternatively, this "cord" may be replaced by a nitinol wire structure that is fixably attached to the injector tubes 15 to provide a (stiffer) metallic penetration limiting member.

Figure 5C:
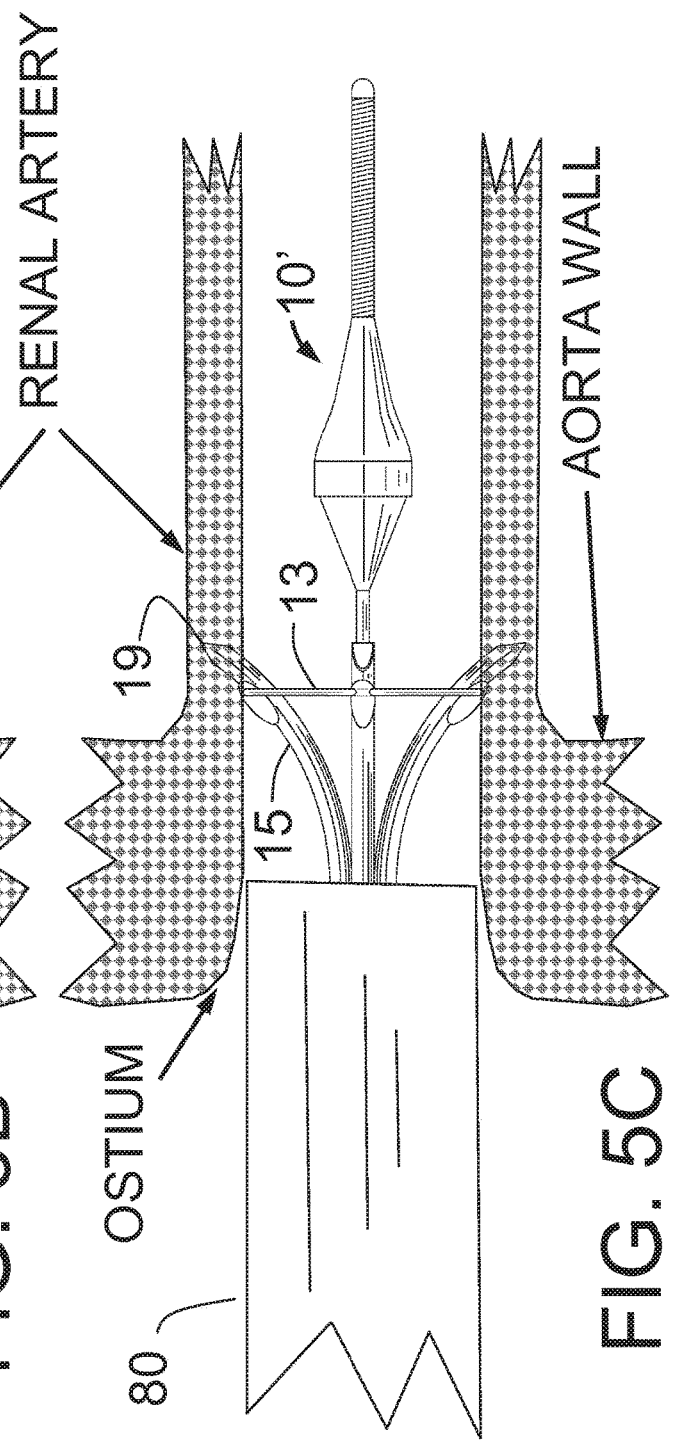
FIG. 5C is a schematic view of the distal portion of the fully open INAS of FIG. 3 with needles fully embedded into the wall of the renal artery to allow the infusion of an ablative substance into the vessel wall.

FIG. 5C is a schematic view of the distal portion of the fully open INAS 10 of FIG. 3 with needles 19 fully embedded into the wall of the renal artery to allow the infusion of an ablative substance into the vessel wall. Although FIG. 5C show the cords 13 fully expanded, it would be typical for them to be slightly less in diameter than their maximum diameter when they engage the wall of the renal artery to limit the penetration of the needles 19. Preferably, the maximum diameter of the INAS 10 system selected for the procedure should be at least 2 to 4 mm greater than the inside diameter of the renal artery. For example, if the renal artery diameter at the desired ablation site is 5 mm in diameter, then a INAS 10 with maximum diameter of 7 to 9 mm should be selected. In the configuration of FIG. 5C, the ablative substance is injected through the needles 19 into the wall of the renal artery. The preferred ablative substance is ethyl alcohol (ethanol), which has historically been used to ablate tissue, particularly nerve tissue in the cardiovascular system. Other agents such as phenol, glycerol, local anesthetic agent(s) such as lidocaine, guenethidine or other cytotoxic and/or neurotoxic agents are also anticipated as possible injectates.

Figure 5D:
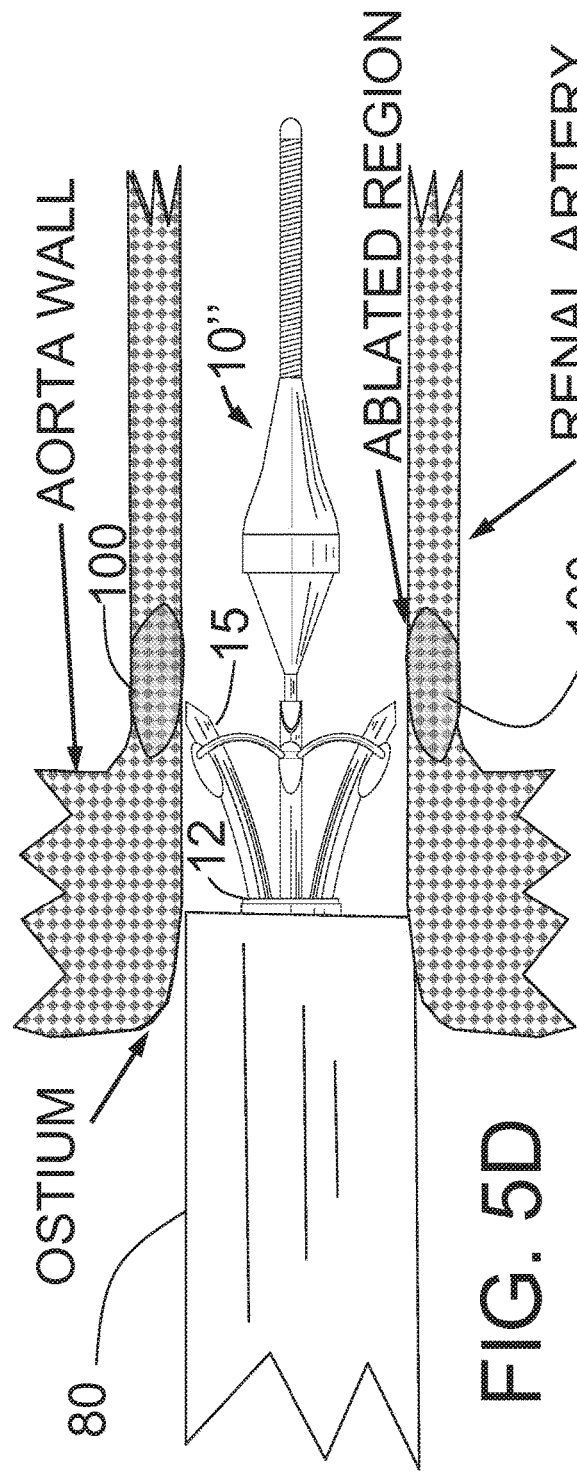
FIG. 5D is a schematic view of the distal portion of the closed INAS as the distal portion of the INAS is being pulled back into the sheath to close the INAS either for subsequent use in the other renal artery or for removal from the body.

FIG. 5D is a schematic view of the distal portion of the closed INAS 10" as its distal portion is being pulled back into the sheath 12 to close the INAS 10" either for subsequent use in the other renal artery or for removal from the body. A shaded area shows the ablated region 100 where the tissue in the wall of the renal artery has been ablated. If the needle depth of penetration is set at a greater depth (e.g. 2.5-3 mm) the ablation zone may be deeper (primarily adventitial) and create less injury to the intimal and medial layers of the renal artery wall than is shown in 5D.

Figure 5E:
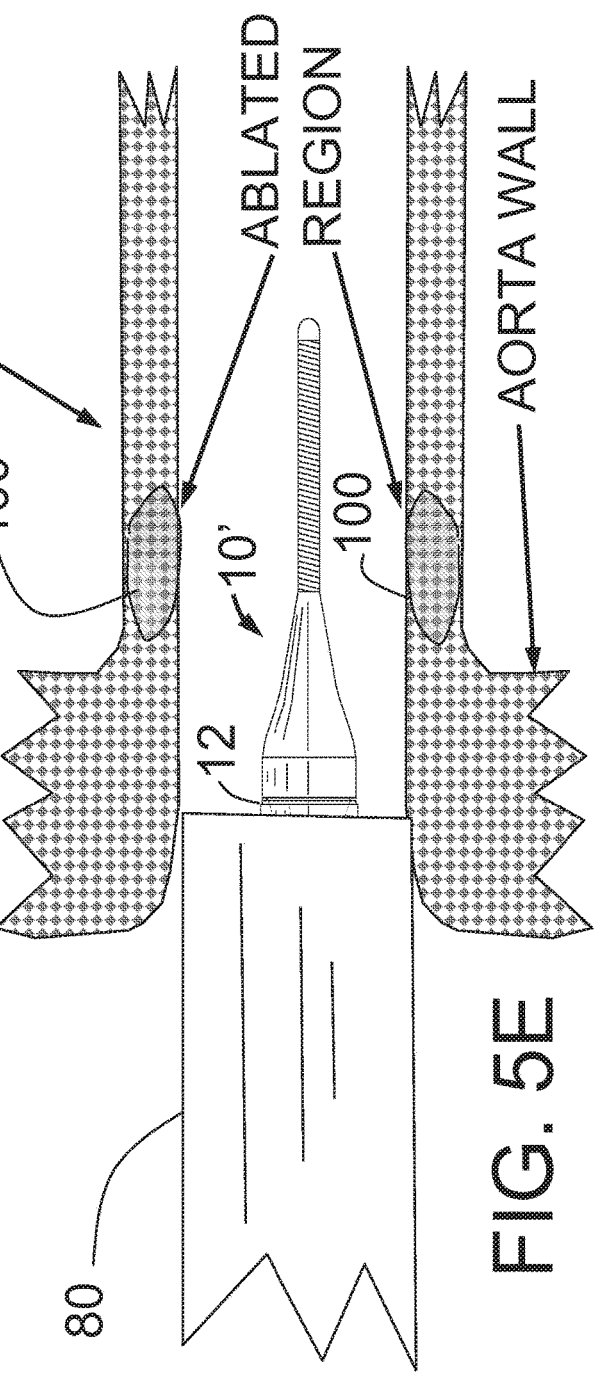
FIG. 5E is a schematic view of the distal portion of the closed INAS of FIG. 2 after it has been closed by retraction of the distal portion of the INAS into the sheath either for subsequent use in the other renal artery or for removal from the body.

FIG. 5E is a schematic view of the distal portion of the closed INAS 10' of FIG. 2 after it has been closed by retraction of the distal portion of the INAS into the sheath 12 either for subsequent use in the other renal artery or for removal from the body.

For this embodiment of the INAS 10, the method of use for hypertension would be the following steps:

1. Remove the sterilized INAS 10 from its packaging in a sterile field, flush the lumen 38 between the outer tube 12 and hypotube 18 with saline.
2. Advance the sheath 12 until the INAS 10' is in its close position.
3. Lock the Tuohy-Borst fitting 30 down onto the hypotube 18 of FIG. 4.
4. Access the aorta via a femoral artery, typically with the insertion of an introducer sheath.
5. Using a guiding catheter 80 of FIGS. 5A through 5E or a guiding sheath with a shaped distal end, engage the first targeted renal artery through the aorta. This can be confirmed with contrast injections as needed.
6. Place the distal end of the INAS 10 in its closed position of FIG. 2 into the proximal end of the guiding catheter 80. There is typically a Tuohy-Borst fitting attached to the distal end of a guiding catheter 80 to constrain blood loss.
7. The closed INAS 10 can be pushed through the opened Tuohy-Borst fitting into the guiding catheter 80.
8. Advance the INAS 10 through the guiding catheter, until the marker band 24 is distal to the distal end of the guiding catheter within the renal artery as shown in FIG. 5A.
9. Pull the sheath 12 back in the proximal direction while holding the Luer fitting 35 and hypotube 18 the proximal end of the INAS 10 fixed. This will allow expansion of the injector tubes 15 against the wall of the renal artery as shown in FIG. 5B.
10. Lock the Tuohy-Borst fitting 30 down on the hypotube 18.
11. With the Tuohy-Borst fitting at the proximal end of the guiding catheter 80 loosened advance the sheath 12 and hypotube 18 locked together pushing the sharpened needles 19 into, or through, the wall of the renal artery as the self-expanding injector tubes 15 continue to expand outward. The injector tubes 15 will stop penetration when penetration limiting member 13 engages the wall of the renal artery thus limiting the penetration of the needles 19 to the desired depth.
12. Attach a syringe or injection system to the Luer fitting 35 of FIG. 4 that provides ablative fluid that will be injected into the wall of the renal artery
13. Inject an appropriate volume of ethanol (ethyl alcohol) or other appropriate cytotoxic fluid, or combination of neuroablative fluids, or heated fluid or steam (e.g., 90-95 degree heated saline solution) from the syringe or injection system through the lumen 36 and out of the needles 19 into the wall of the renal artery. A typical injection would be 1-10 ml. This should produce a multiplicity of intersecting volumes of ablation (one for each needle) that should create a torroid of ablated tissue around the circumference of the renal artery as shown as the ablated regions shown in FIGS. 5D and 5E. Contrast and/or an anesthetic agent such as lidocaine can be injected before or at the same time as the ablative fluid.
14. Loosen the Tuohy-Borst fitting 30 and while holding the Tuohy-Borst fitting 30 and sheath 12 fixed, pull the Luer 35 with hypotube 18 in the proximal direction until the expandable tubes 15 with needles 19 are fully retracted back into the distal end of the sheath 12 and the marker bands 27 and 25 are next to one another. This is shown in FIGS. 5D and 5E.
15. In some cases, one may advance the INAS 10 again into the renal artery, rotate it between 20-90 degrees and then repeat the injection to make an even more definitive volume of ablation. This would be advantageous if the INAS 10 has fewer than 4 injector tubes and should not be needed with the 4 injector tubes shown in herein.
16. The same methods as per steps 8-15 can be repeated to ablate tissue around the other renal artery during the same procedure.
17. Remove the INAS 10 in its closed position from the guiding catheter. Being in the closed position, the needles 19 are enclosed and cannot harm the health care workers, or expose them to blood borne pathogens.

18. Remove all remaining apparatus from the body.

A similar approach can be used with the INAS 10, to treat atrial fibrillation through a guiding catheter inserted through the septum into the left atrium with the wall of the target vessel being the wall of one of the pulmonary veins.

Figure 6:
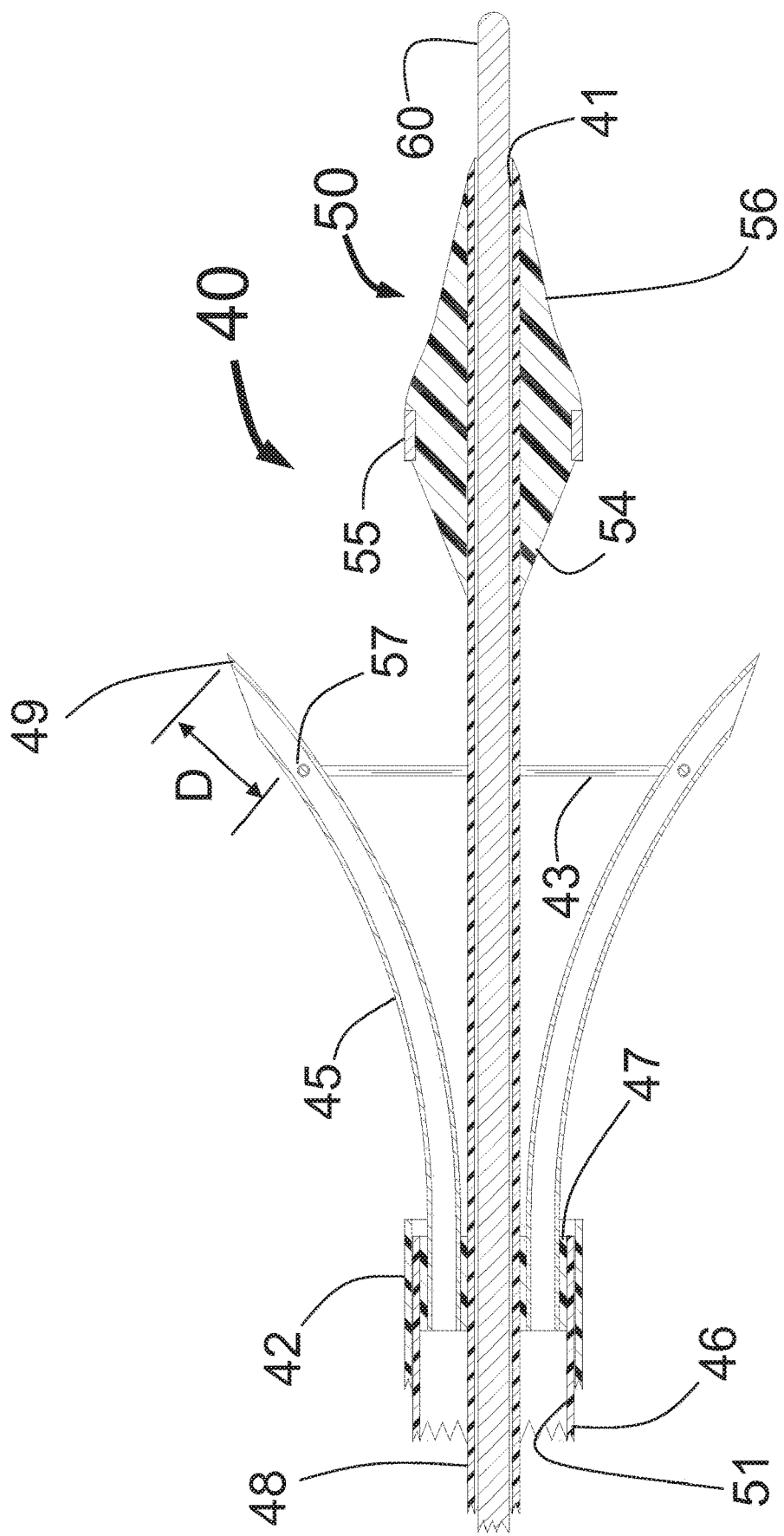
FIG. 6 is a longitudinal cross section drawing of the embodiment of the INAS that is delivered over a separate guide wire.

FIG. 6 is a longitudinal cross section drawing of the distal portion of another embodiment the present invention Vascular Nerve Ablation System (INAS) 40 that is delivered over a separate guide wire 60. FIG. 6 shows the INAS 40 in its fully open position with the self-expanding injector tubes 45 with distal ends sharpened to form needles 49 open to their maximum diameter. Flexible cords 43 connect the injector tube 45 and act as a penetration limiting member to prevent the distal tip of the needles 49 from penetrating more than a maximum distance D into a vessel wall. Unlike the cord 13 of FIG. 1, the cords 43 are fed though holes 57 in the sides of each injector tube 45 a distance D from the distal end. A drop of adhesive (not shown) can be used to seal the holes and prevent leakage of the ablative substance or solution during injection into a vessel wall.

A sheath 42 is shown in its position where it has been pulled back to allow full expansion of the injector tubes 45. There are 4 injector tubes 45 in this embodiment of the INAS 40 although as few as 2 and as many as 12 are envisioned. The distance D can be between 0.2 and 2 mm with the optimal being about 0.5-1 mm.

The proximal end of the injector tubes 45 are held by a manifold 47 that is attached inside the distal end of the outer tube 46 and the inner tube 48. An injection lumen 51 lies between the inner tube 48 and outer tube 46 proximal to the manifold 47. Ablative material injected through the injection lumen 51 will flow into the proximal ends of the injector tubes 45 and then out of the injection needles 49 into one or more layers of the blood vessel and/or into the volume of tissue just outside the vessel wall.

Figure 7:
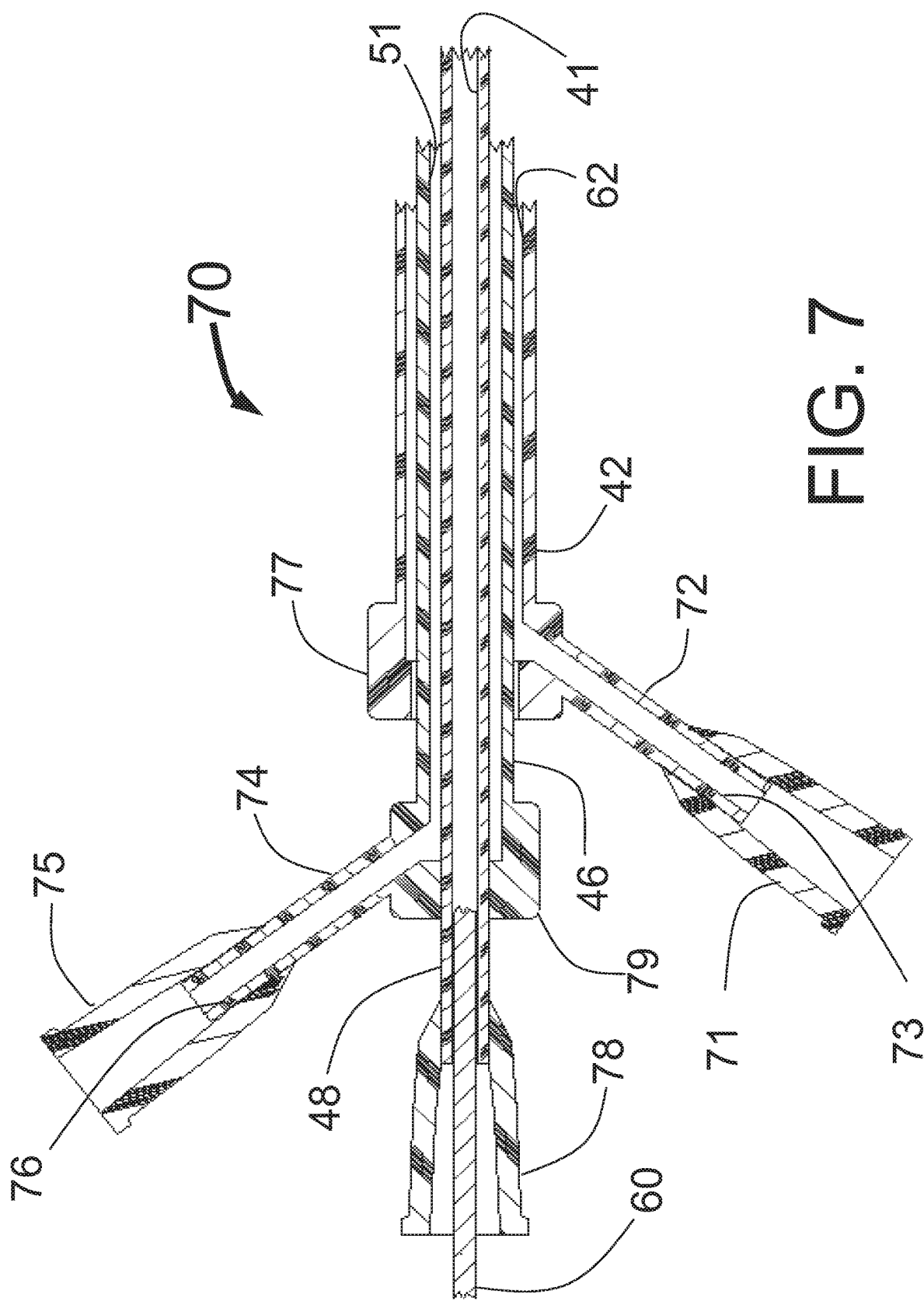
FIG. 7 is a longitudinal cross sectional drawing of the proximal end of an over-the-wire embodiment of the INAS of FIG. 6.

The distal section 50 of the INAS 40 that is coaxially attached to the distal section of the inner tube 48 includes the tapered flexible tip 56, radiopaque maker 55 and sheath engagement section 54 that assures that the distal portion of the INAS 40 will properly pull back into the sheath 42 following use of the INAS 40 to ablate tissue in a vessel and the human body. The guide wire 60 can be advance and retracted in the longitudinal direction inside of the guide wire lumen 41 that lies inside of the inner tube 48. The INAS 40 can be configured either as an over-the-wire or a rapid exchange device. If over-the-wire, the guide wire lumen 41 inside of the inner tube 48 runs all the way to the proximal end of the INAS 40 as is shown in FIG. 7. If a rapid exchange configuration is used then the guide wire would exit from the INAS 40 and run external to the outside of the INAS 40 for some portion of the length of the INAS 40. If a rapid exchange is used then a slot will be needed in the sheath 42 to allow for the sheath 42 to move longitudinally with respect to the rest of the INAS 40. The proximal end of the rapid exchange configuration would be identical to that of the fixed wire INAS 10 of FIG. 4. The guide wire would typically run outside of the body of the INAS 40 for at least the most proximal 10 cm with the preferred embodiment having the guide wire exit through the side of the outer tube 46 and sheath 42 between 5 and 15 cm from the distal end of the INAS 40.

FIG. 7 is a longitudinal cross sectional drawing of the proximal end 70 of an over-the-wire embodiment of the INAS 40 of FIG. 6. The inner tube 48 has a Luer fitting 78 attached to its proximal end. The guide wire 60 can be advanced through the guide wire lumen 41 inside of the inner tube 48. The proximal end of the outer tube 46 is attached to the hub 79 that is sealed against the inner tube 48, forming the injection lumen 51 between the inner tube 48 and outer tube 46. A side tube 74 with lumen 76 connects into the hub 79 with a Luer fitting 75 attached to the proximal end of the side tube 74. A syringe or other injection device can be attached to the Luer fitting 75 to inject an ablative substance or solution through the lumen 76 into the injection lumen 51 into the injector tube 45 of FIG. 6 and out of the ends of the injection needles 49 into a vessel wall. The proximal end of the sheath 42 connects to the hub 77 that acts as a handle to slide the sheath 42 coaxially over the outer tube 46 to open and close the INAS 40 of FIG. 6. A side tube 72 with lumen 73 connects into the hub 77. A Luer fitting 71 it attached to the proximal end of the side tube 72 to allow the lumen 62 between the sheath 42 and the outer tube 46 to be flushed with saline solution before introduction of the INAS 40 in to the human body. While the hub 77 shown here is a plastic member, it is envisioned that a Tuohy-Borst fitting such as the Tuohy-Borst fitting 30 of FIG. 4 could be used here and could be advantageous as it would allow one to lock the sheath 42 in position onto the outer tube 46 during insertion and removal from the body so that the distal end of the sheath 42 would remain in its most distal position protecting the injection needles 49 and protecting health care workers from exposure to needle stick injury.

Figure 8:
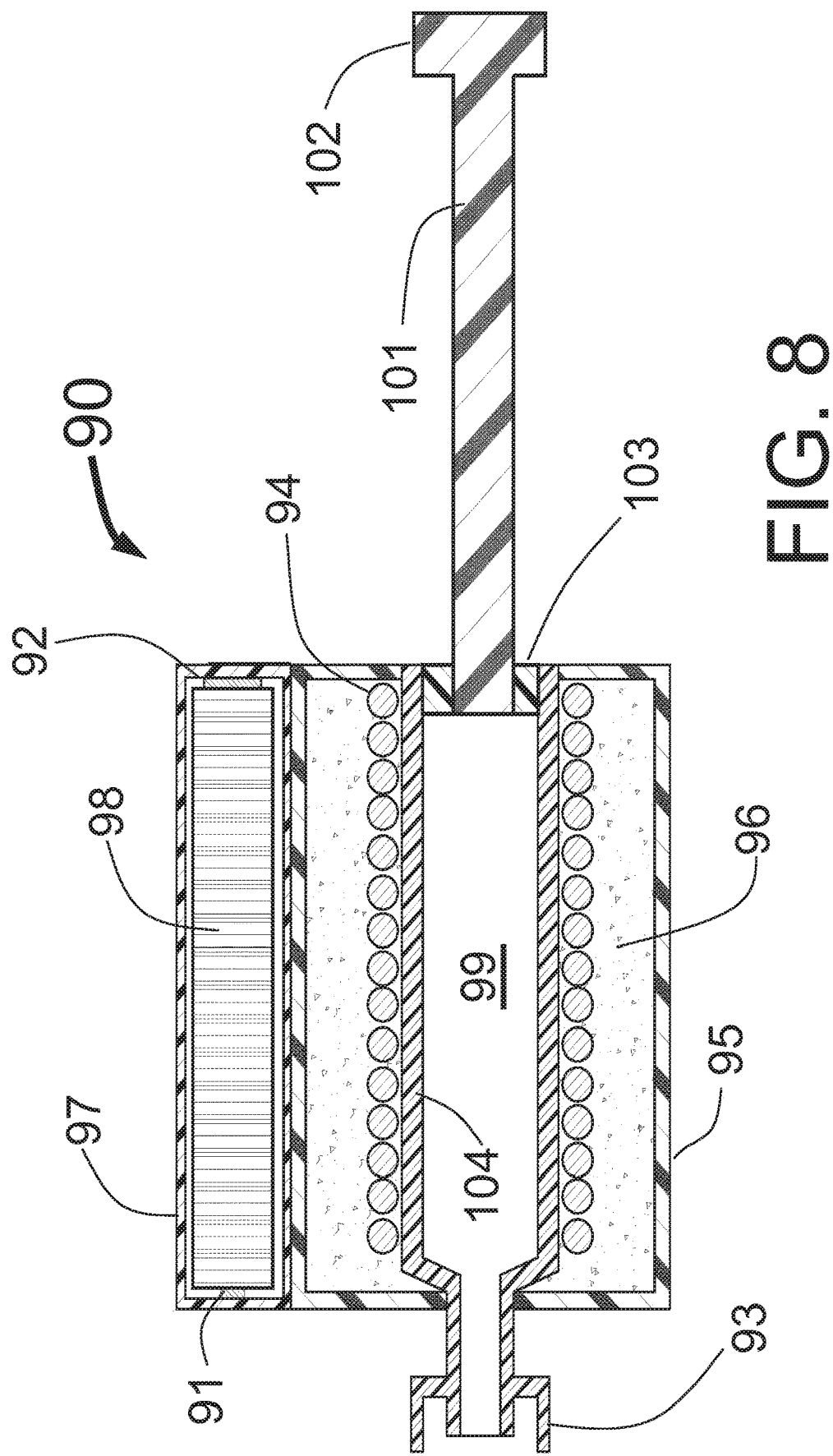
FIG. 8 is a longitudinal cross section drawing of an injector capable of delivering a heated ablative solution into the INAS of FIGS. 1-4.

FIG. 8 is a longitudinal cross section of a disposable injector 90 for use in providing ablative fluid heated to a preset temperature for injection through the INAS 10 of FIGS. 1-5C to ablate tissue in a human body. The injector 90 includes a syringe 104 with fluid storage volume 99 and female Luer fitting 93 that would typically attach to a standard stopcock (not shown) the stopcock being connected to the male Luer fitting 35 at the proximal end of the INAS 10 of FIGS. 1-4. It is also envisioned that a stopcock could be provided with either the injector 90 or INAS 10 or integrated into either. The syringe 104 is surrounded by the heating coil 94 which is contained within the case 95 filled with heat insulation 96. The power for the heating coil 94 comes from the battery 98 with positive terminal 91 and negative terminal 92 housed in the battery case 97. A moveable plunger 101 with handle 102 and distal sealing gasket 103 is used to inject the heated ablative fluid in the volume 99 through the Luer fitting 93 into the INAS 10 injector lumen 21 of FIG. 4 where it will then flow out through the injector needles 19 of FIGS. 1 and 3 into the tissue as shown in FIG. 5C. The injector 90 may include closed loop electronics with either a display of the temperature or one or more LEDs that let the user know when the ablative fluid in the syringe 104 is at the desired temperature. The injector 90 could be manufactured for a single preset temperature or be adjustable to more than one temperature. While FIG. 8 shows a manual injection plunger 101, it is also envisioned that a fluid pump or mechanical system to depress the plunger could be integrated into the injector 90. The use of heated fluid to abate tissue may be either effective by having a normally benign substance like normal saline heated to the point where the heat causes the tissue ablation or the heat may act to improve the ablative ability of a fluid such as alcohol that is normally ablative at room or body temperature.

Figure 9:
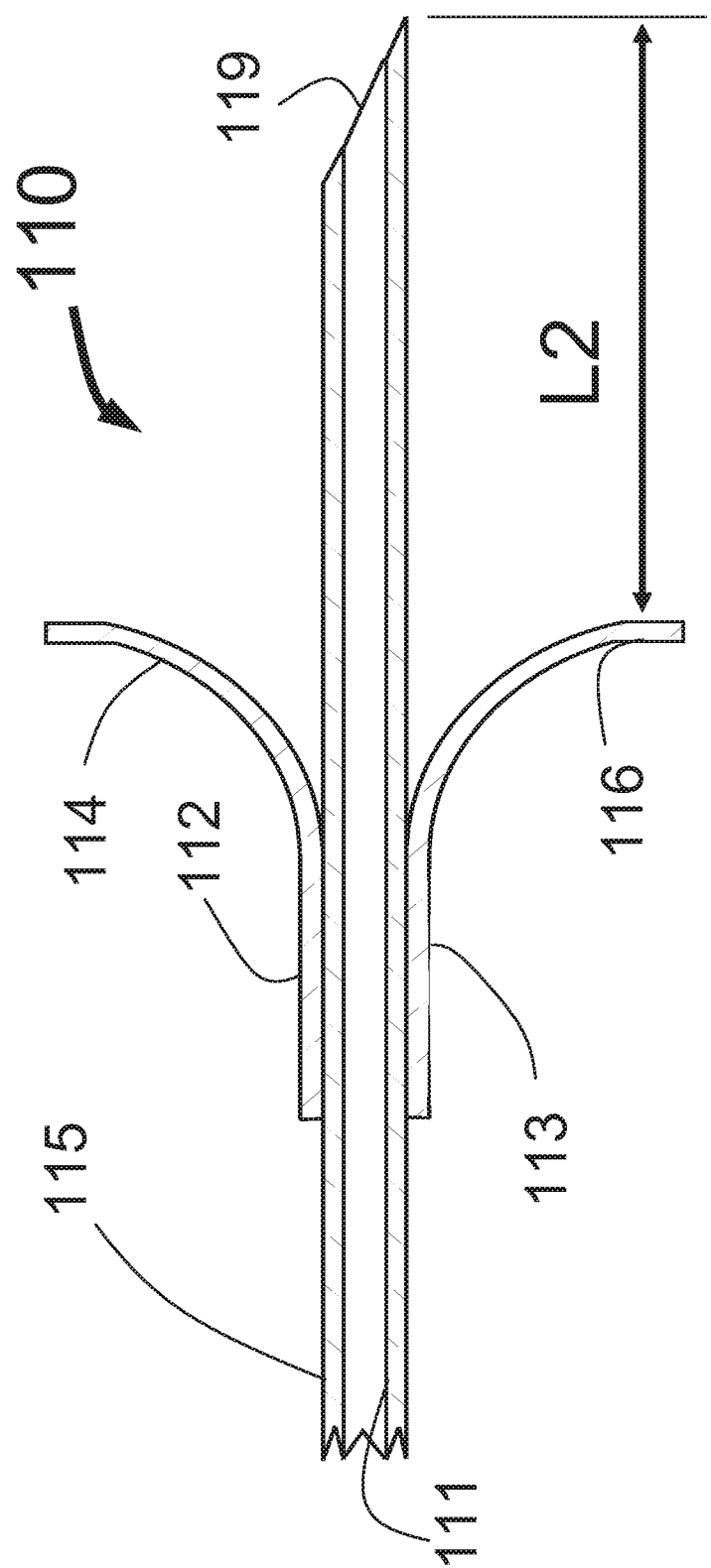
FIG. 9 is a longitudinal cross section drawing of the proximal section of an injection needle showing longitudinal welded wire penetration limiting members.

FIG. 9 is a longitudinal cross section drawing of the proximal section of an injection needle 110 with lumen 111 and distal end 119, showing attached longitudinal memory metal wire penetration limiting members 114 and 116 with proximal portions 112 and 113 respectively. These proximal portions 112 and 113 are attached (glued, welded or brazed) to the outside 115 of the needle so that when the needles 110 are released from inside of the sheath 12 of FIGS. 1-4 the distal portion of the wires 114 and 116 will assume their memory state as shown in FIG. 9 forming a member that will limit penetration of the needle tip 119 to approximately a preset distance L2. Since most arteries have a similar thickness, the distance L2 can be set to ensure the ablative fluid injected through the needle lumen 111 will emerge in the appropriate volume of tissue. Selection of the appropriate volume can be set by different values of L2 such that the injection can be set to be in the media of the artery, the adventitia of the artery or outside the adventitia of the artery. While FIG. 9 shows two wires 114 and 116, one wire would also function to limit penetration or 3 or more wires could also be used. Ideally the wire(s) would be attached to the outside of the needle 115 on the sides circumferentially of the needle and not on the inside or outside where the wires 114 and 116 would increase the diameter of the closed INAS 10 of FIGS. 1-4 before the sheath 12 is pulled back to deploy the needles.

It is also envisioned that an injector designed to deliver a super-cooled ablative fluid into the INAS of FIGS. 1-4 could also be appropriate for this application.

An important aspect of the present invention is the circumferential delivery of the ablative fluid with respect to the vessel wall. Such delivery from one or more injection egress points must attack the nerve tissue circumferentially and at the correct depth to ensure efficacy, and ideally to minimize injury to the healthy and normal cellular structures of the intimal and medial layers. The circumferential delivery in a circular or helical pattern can be handled as described above in three different ways.

1. Injection into the vessel wall at three or more points around the circumference of the vessel
2. Injection into the space outside of wall of the vessel—although this can be accomplished by a single needle/egress point, this is best done with at least two egress points so that the needles can be kept small so as to allow the vessel wall to reseal as the needles are retracted.
3. Injection into the inside to fill an annular space and delivery the ablative fluid circumferentially to the inside surface of the vessel.

Figure 10:
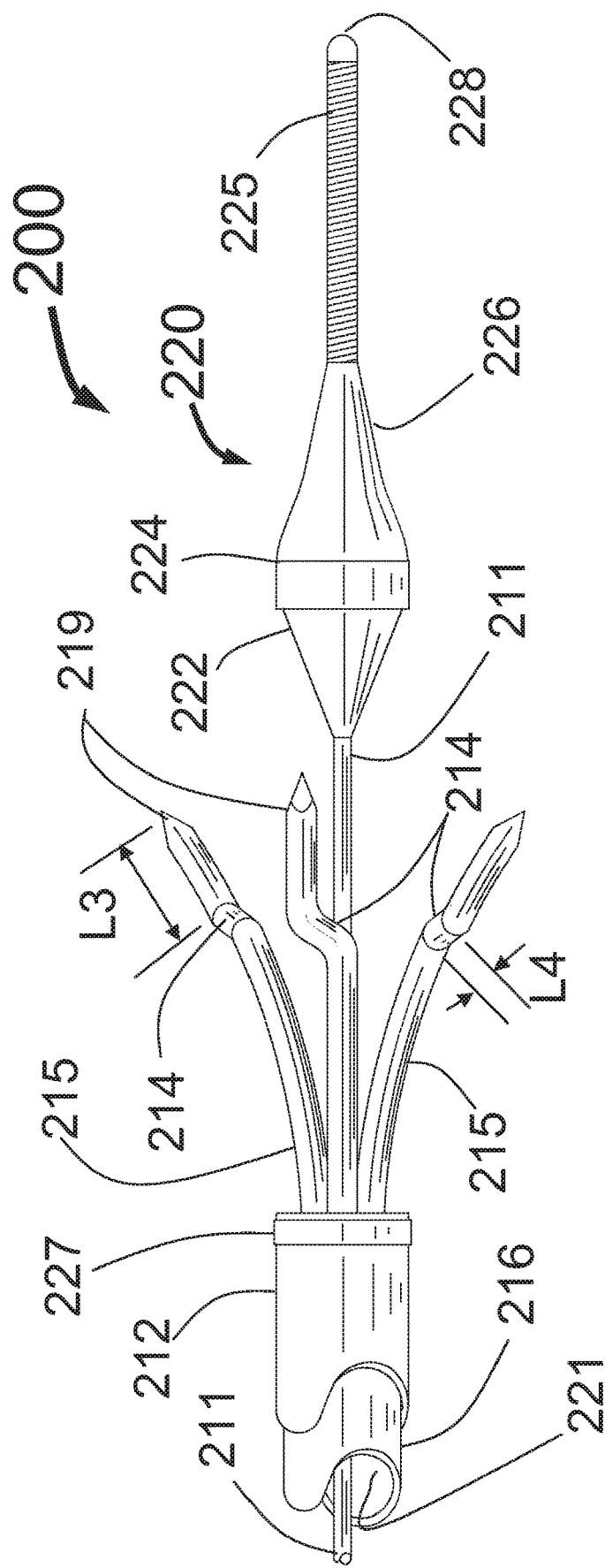
FIG. 10 is a schematic view of the proximal section of another embodiment of the present invention that delivers an ablative fluid circumferentially to the inside of a target vessel.

FIG. 10 is a schematic view of yet another embodiment of the distal portion of the present invention Intravascular Nerve Ablation System (INAS) 200 in its fully open position having a fixed guide wire 225 with tip 228 at its distal end. FIG. 10 shows the INAS 200 in its fully open position with the self-expanding injector tubes 215 with distal ends sharpened to form injection needles 219 open to their maximum diameter. In this embodiment the injector tubes 215 each have a double bend or kink 214 having length L4 in the circumferential direction. The kinks 214 act as a penetration limiting member to prevent the distal tip of the needles 219 from penetrating more than a maximum distance L3 into a vessel wall.

A sheath 212 with radiopaque marker 227 is shown in FIG. 10 in its position where it has been pulled back to allow full expansion of the injector tubes 215. There are 3 injector tubes 215 in this embodiment of the INAS. The distal section 220 of the INAS 200 includes the fixed distal wire 225, tapered flexible tip 226, radiopaque maker 224 and sheath engagement section 222 that assures that the distal portion will properly pull back into the sheath 212 following use of the INAS 200 to ablate tissue in a vessel of the human body.

Also shown in FIG. 10 are the outer tube 216 with injection lumen 221 and core wire 211. The INAS 200 of FIG. 10 would be used in the same way as the INAS 10 of FIGS. 1 through 5E with the difference being the use of the kinks (double bends) 214 as the penetration limiting members. The kinks 214 being integrated into the injector tubes 215 as compared with the penetration limiter of FIGS. 1-5E which are attached to the injector tubes. Adding the kinks 214 should be a matter of setting a double bend into the shape of the memory metal (e.g. NITINOL) tubing used to form each of the injector tubes 215 that have sharpened ends that form the injection needles 219. In this embodiment the injector tubes themselves limit the penetration into the wall of a target vessel. Processes for shaping and heat treating NITINOL tubing to set the memory are well known.

The present invention has discussed use of the INAS for ablating tissue in the human body. It may also have merit for intravascular injection of any fluid or medication. The ability to limit the depth of penetration allows it to inject any fluid selectively into the media, adventitia or outside of the adventitia of a blood vessel. It is also envisioned that the use of the double bend penetration limiting member concept of FIG. 10 could be applied to any application where fluid injection is required at a preset distance into human tissue.

The term circumferential delivery is defined here as at least three points of simultaneous injection spaced circumferentially within a vessel wall, or circumferential filling of the space outside of the adventitial layer (outer wall) of a blood vessel.

Figure 11:
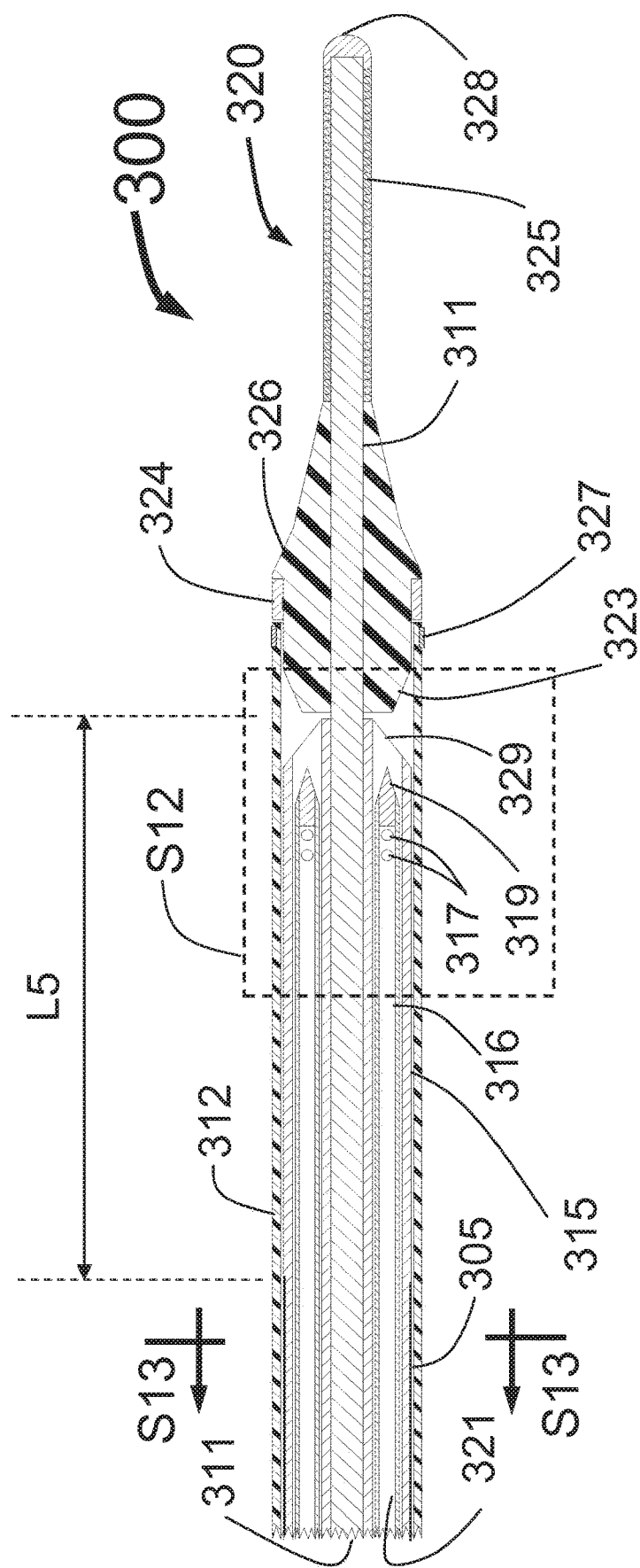
FIG. 11 is a longitudinal cross section of another embodiment of the present invention INAS in its closed position having four injector tubes that can slide within four guide tubes. The injector tubes have sharpened needles having injection egress ports at the distal end of each injector tubes.

FIG. 11 is a longitudinal cross section of the another embodiment of the present invention INAS 300 in its closed position having four injector tubes 316 that can slide within four guide tubes 315 having expandable distal portions. The injector tubes 316 with sharpened needles 319 have injection egress ports 317 near the distal end of each injector tube 316. A sheath 312 with distal radiopaque marker band 327 encloses the guide tubes 315 with coaxial injector tubes 316. The injector tubes 316 have injection lumens 321. The distal end of each of the guide tubes 329 are tapered to provide a surface that will be approximately parallel to the vessel wall when the guide tubes 315 expand outward during deployment. The distal portion of the guide tubes 315 having a length L5 are set in an expanded memory shape and as shown in FIG. 11 are constrained by the sheath 312 to prevent expansion. The four guide tubes 315 are not attached or connected to the core wire 311 over the distance L5. Proximal to the distance L5 the guide tubes 315 are attached or connected to the core wire 311 with the preferred embodiment shown in FIG. 13 where the core wire 311 and four guide tubes 315 are embedded in a plastic cylinder 305.

The INAS 300 distal end has a tapered section 326 attached to a distal shapeable fixed guide wire 320 with wire wrap exterior 325, core wire 311 and tip 328. The tapered section 326 includes a radiopaque marker 324 and proximal taper 323 to facilitate closing the sheath 312 over the proximal section 323 following deployment of the INAS 300 to inject ablative fluid into a vessel wall.

FIG. 12 is an enlargement of the area S12 of the INAS 300 of FIG. 11 showing guide tubes 315 located coaxially inside of the sheath 312. The distal portion of the injector tubes 316 having sharpened needles 319, lumens 321 and injection egress ports 327 are located coaxially inside of the distal portion of the guide tubes 315 with tapered distal ends 329. All or a portion of the needles 319 or the entire injector tube(s) may be made of a radiopaque material such as tantalum, platinum or gold. It is also envisioned that the ends of the needles may be coated or plated with a radiopaque material such as gold or that a platinum insert is placed into the distal tip of the injection tube prior to sharpening the tip into a cutting needle. Also shown are the core wire 311 and the proximal section 323 of the tapered section 326. It is also envisioned that a distal portion including the distal end 329 of the guide tubes 315 may also be made of, coated or plated with a radiopaque material such as gold.

FIG. 13 is a circumferential cross section at S13-S13 of the INAS 300 of FIG. 11 clearly showing the four guide tubes 315 attached to the outside of the core wire 31. The injector tubes 316 with injection lumens 321 are located coaxially inside of the guide tubes 315. The injection tubes 316 are free to slide in the longitudinal direction within the lumens of the guide tubes 315. The injection tubes 316 could also be formed from nitinol and pre-shaped to parallel the curved distal shape of the guide tubes 315 to enhance the coaxial movement of the injector tubes 316 within the guide tubes 315. The guide tubes 315, injection tubes 316 and core wire 311 lie coaxially within the sheath 312 which is free to slide over these parts. It is also shown how the guide tubes 315 and core wire 311 are be embedded in plastic 305 to better hold the parts together or they could be joined by welding, brazing of use of an adhesive. The use of the plastic 305 also allows a cylindrical surface to which the proximal portion of the sheath 312 can seal to allow flushing of the space between the inside of the sheath 312 and the outside of the plastic 305 with saline before the start of device use.

Figure 14:
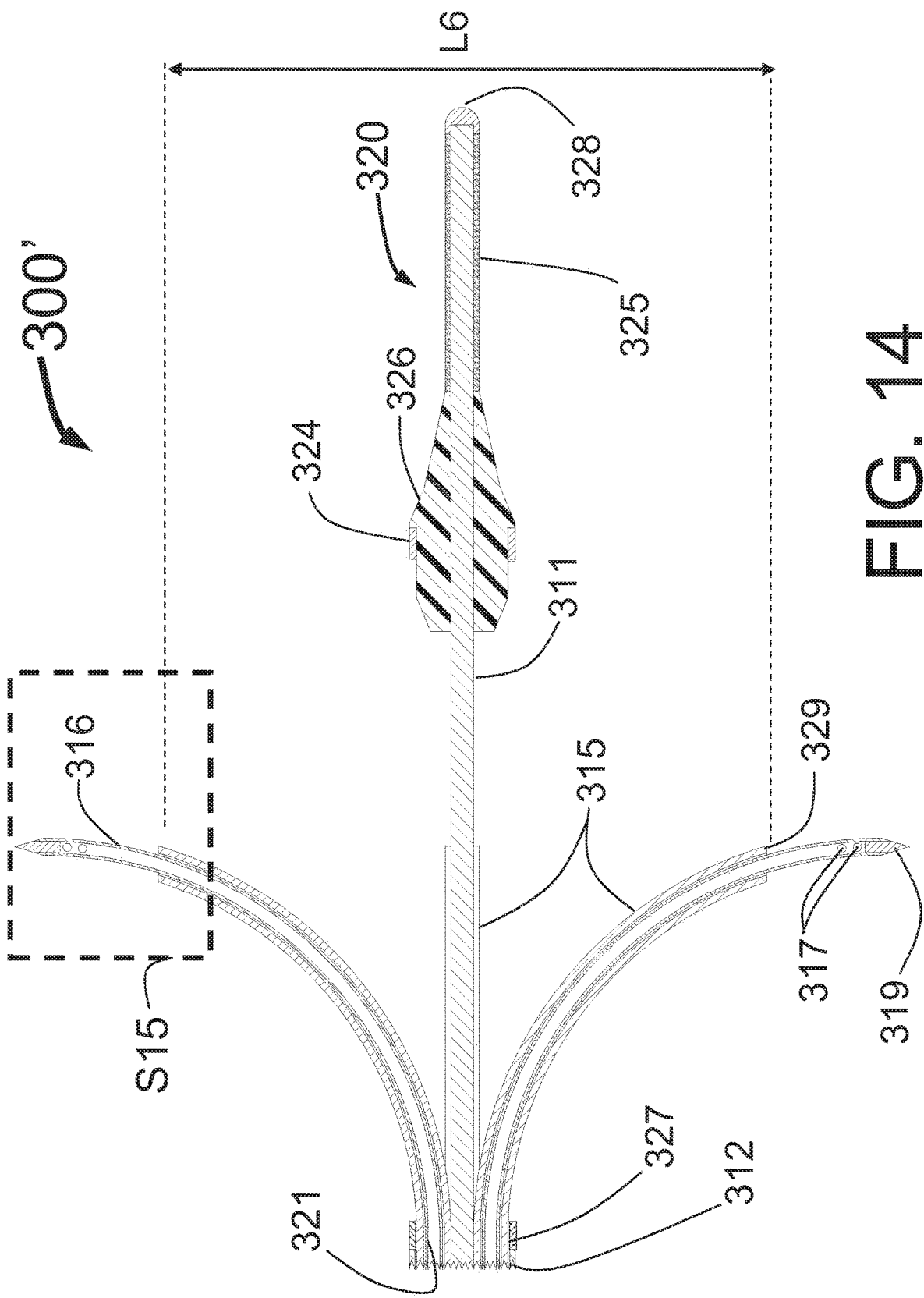
FIG. 14 is a longitudinal cross section of the expanded distal portion of the INAS.

FIG. 14 is a longitudinal cross section of the expanded distal portion of the INAS 300' in the fully open configuration with the injection tubes 316 shown advanced beyond the distal end of the guide tubes 315. The distal end of the injector tubes 316 has the sharpened needles 319 with injection egress ports 317.

In this configuration the sheath 312 has been pulled back to allow the guide tubes 315 to expand outward. The guide tubes 315 are typically made from a memory metal such as NITINOL. The injector tube 316 may be made from any metal, such as 316 surgical grade stainless steel, NITINOL or a radiopaque metal such as tantalum or platinum. If the elements 315 and 316 are not fabricated from a radio-opaque metal it is envisioned that distal portion of the injector tube(s) 316 and guide tube(s) 315 would be coated with a radio-opaque material such as gold, typically at or near the distal end of the tube(s) or a piece of radiopaque material may be used to form or be located near the sharpened needles 319 at the distal end of the injector tubes. The diameter L6 denotes the memory configuration for the fully open guide tubes 315. For use in the renal arteries, L6 would typically be between 3 and 10 mm with 8 mm being a best configuration if only one size is made as very few renal arteries are larger than 7 mm diameter. Also shown in FIG. 14 are the distal ends 329 of the guide tubes 315 that in the fully open configuration are approximately parallel to the longitudinal axis of the INAS 300'. The distal portion of the INAS 300' has the tapered section 326 attached to the fixed guide wire 320 with tip 328, outer layer 325 and core wire 311.

Figure 15:
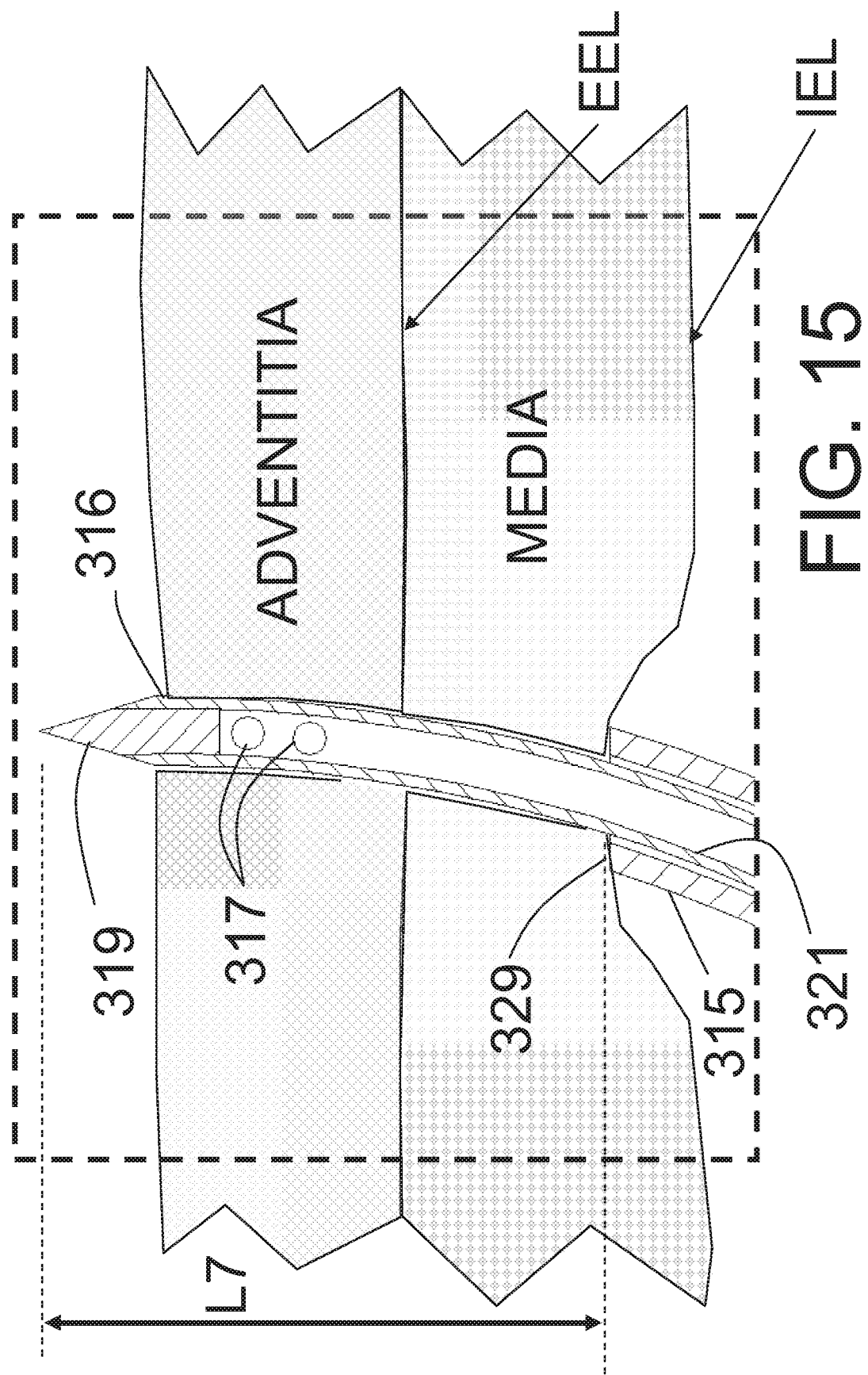
FIG. 15 is an enlargement of the area S15 of FIG. 14.

FIG. 15 is an enlargement of the area S15 of FIG. 14 as it would appear with the distal end of the injector tube 316 with lumen 321 and distal needle 319 fully advanced beyond the distal end 329 of the guide tube 315. Also shown in FIG. 15 is the arterial wall with internal elastic lamina (IEL), Media, External Elastic Lamina (EEL) and adventitia. FIG. 14 shows that the injection egress ports 317 are placed into the heart of the adventitia.

An important feature of the present invention INAS 300 is that the penetration depth for injection through the injection egress ports is adjustable so that any of the following can be accomplished.
1. Injection into the media
2. Injection into the media and adventitia by positioning one of the injection egress holes in each.
3. Injection into the adventitia as shown in FIG. 15,
4. Injection into both the adventitia and the volume outside of the adventitia and
5. Injection only into the volume outside the adventitia.

Specifically, the distance L7 that the tip of the needle 319 extends beyond the end 329 of the guide tube 315 can be adjusted using the apparatus in the proximal end of the INAS 300.

Figure 16:
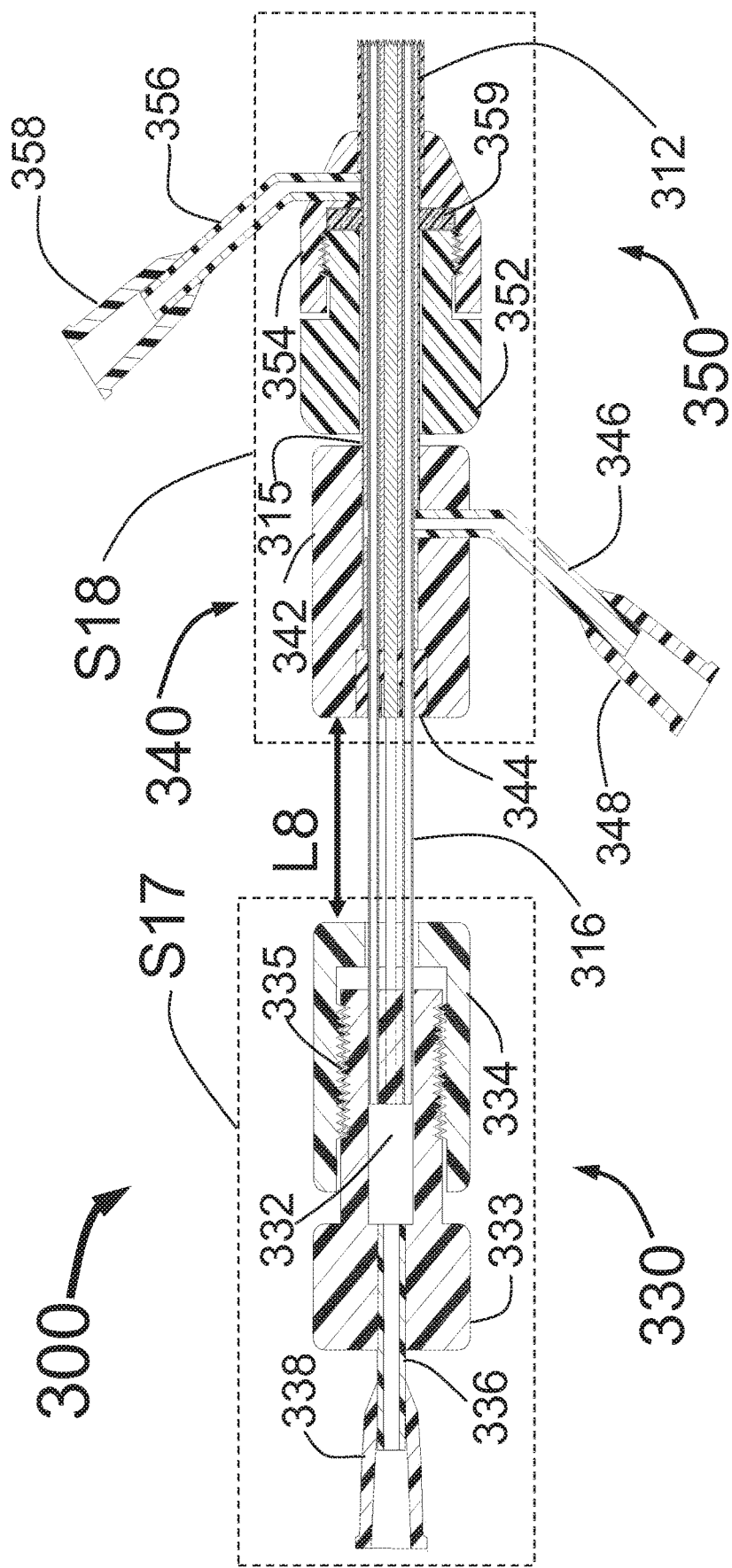
FIG. 16 is a longitudinal cross section of the proximal end of the INAS of FIGS. 11-15.

FIG. 16 is a longitudinal cross section of the proximal end of the INAS 300 of FIGS. 11-15. Three handles, the proximal injection handle 330, the central guide tube handle 340 and the distal sheath control handle 350 allow the relative longitudinal movement of the sheath 312, guide tubes 315 and injector tubes 316. The position shown for FIG. 16 has the sheath control handle 350 in its most proximal position which would indicate the sheath 312 has been fully pulled back in the proximal direction which would allow the guide tubes 315 to expand outward as shown in FIG. 14. The gap with distance L8 between the injection handle 330 and the guide tube handle 340 can be adjusted using the screw adjustment piece 334 with screw threads 335 that allow it to move with respect to the proximal portion 333 of the injection handle 330. The gap L8 as set will limit the penetration of the needles 319 and injection egress ports 317 of the injector tubes 316 into the wall of the target vessel. Ideally, a scale can be marked on the proximal portion 333 of the proximal injection handle 330 so that the medical practitioner can set the gap L8 and thus adjust the penetration distance. A luer fitting 338 with access tube 336 is the port for ablative fluid injection into the handle central lumen 332 which is in fluid communication with the lumens 321 of the injector tubes 316.

The central guide tube handle 340 includes an outer portion 342, a sealing member 344 that seals the distal portion of the core wire 311 to the outer portion 342 and provides four holes through which the four injector tubes 316 can slide into the proximal ends of the guide tubes 315. A Luer fitting 348 with access tube 346 provides access to the space between the injector tubes 316 and the guide tubes 315 through holes in the guide tubes 347.

The distal sheath control handle 350 includes a distal portion 354 attached to the outside of the sheath 312 with Luer fitting 358 and side tube 356 providing access to the lumen under the sheath 312 to allow it to be flushed with saline before the procedure begins. The handle 350 also has proximal portion 352 and elastic washer 359 that is compressed by screwing the proximal portion 352 into the distal portion 354 to lock the position of the sheath 312 with respect to the guide tubes 315.

Figure 17:
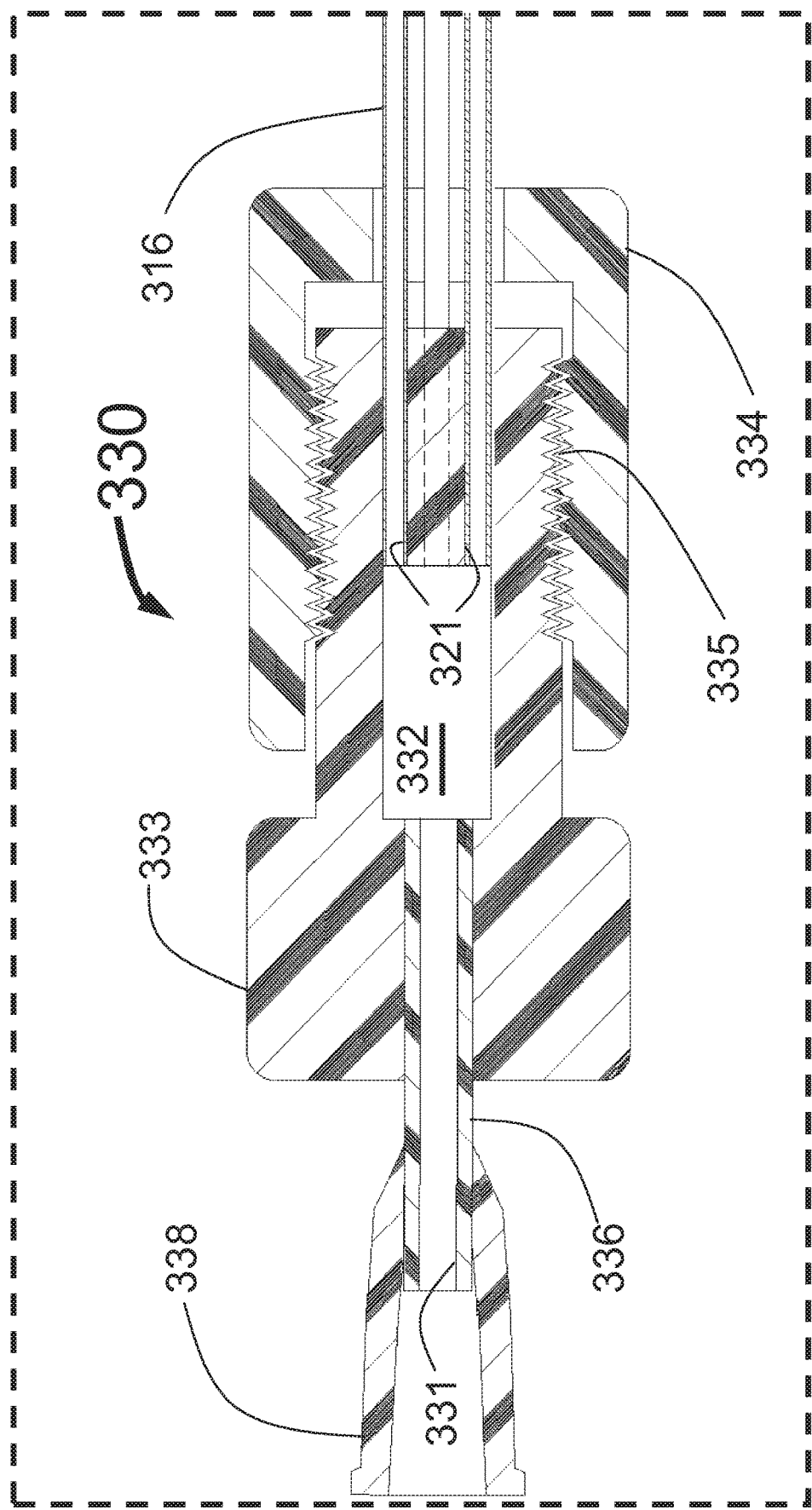
FIG. 17 is an enlargement of the area S17 of FIG. 16.

FIG. 17 is an enlargement of the area S17 of FIG. 16 showing the injection handle 330 with proximal Luer fitting 338 attached to the side tube 336 with lumen 331. The proximal portion 333 is sealed against the outside of the side tube 336 and also seals against the outside of the four injector tubes 316. This sealing can be by an adhesive or by molding or forming the proximal piece onto the tubes 336 and 316. The lumen 331 of the side tube 336 is in fluid communication with the central lumen 332 of the proximal portion 333 which is in fluid communication with the lumens 321 of the injector tubes 316. Thus an ablative fluid injected through the Luer 338 will flow into the lumens 321 of the injector tubes 316 and will emerge through the injection egress ports 317 shown in FIG. 15 into the tissue in or near the wall of the target vessel. The screw threads 335 on both the proximal portion 333 and screw adjustment piece 334 of the injection handle 330 allow adjustment of the gap L8 of FIG. 16. The gap L8 as set will limit the penetration of the needles 319 and injection egress ports 317 of the injector tubes 316 into the wall of the target vessel. Ideally, a scale can be marked on the proximal portion 333 of the injection handle 330 so that the medical practitioner can set the gap L8 and thus adjust the penetration distance.

Figure 18:
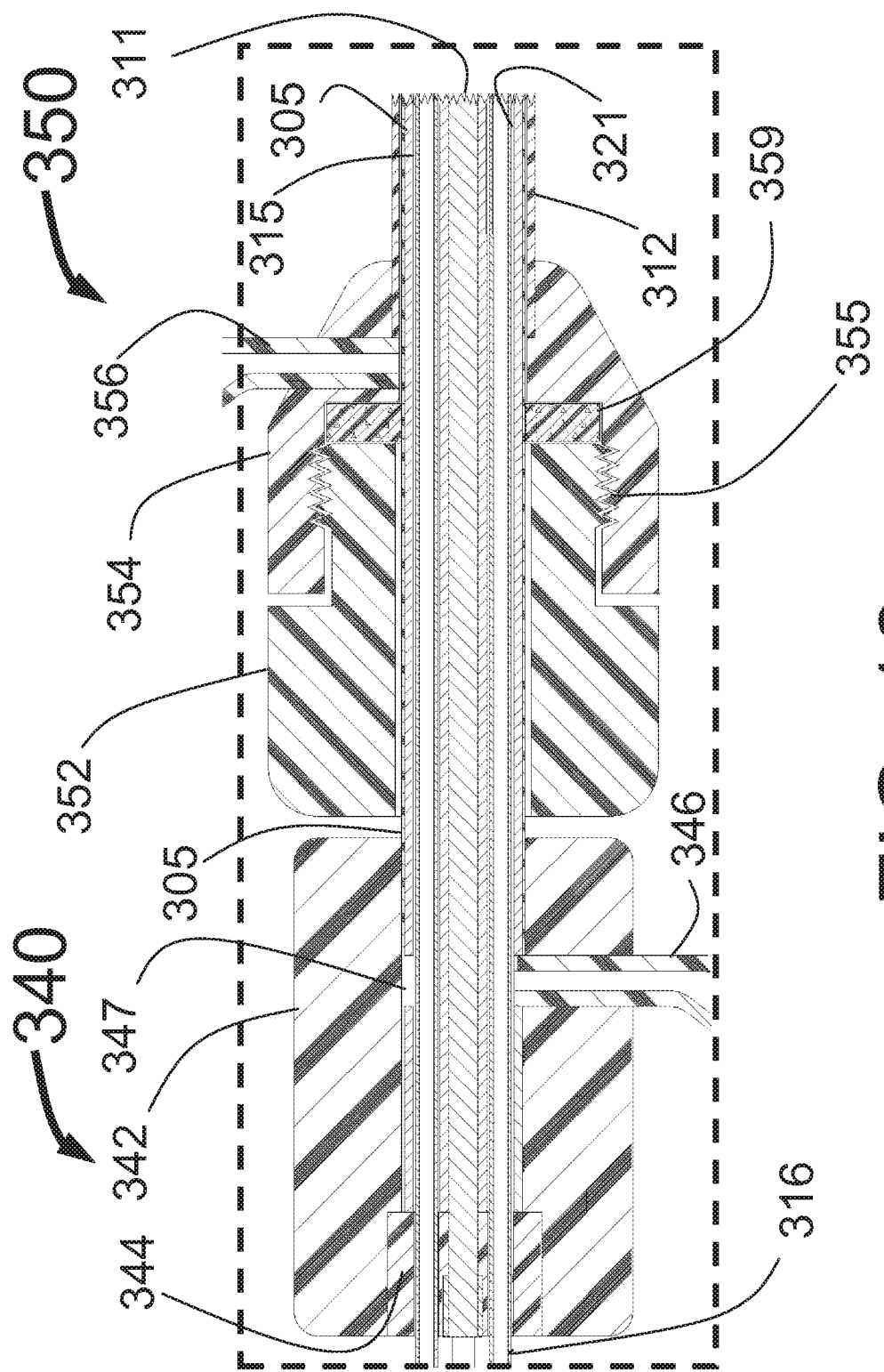
FIG. 18 is an enlargement of the area S18 of FIG. 16.

FIG. 18 is an enlargement of the area S18 of FIG. 16 showing the central guide tube handle 340 and the sheath control handle 350.

The central guide tube handle 340 includes an outer portion 342, a sealing member 344 that attaches the distal portion of the guide tubes 315 and core wire 311 to the outer portion 342. The outer portion 342 seals against the plastic 305 in which the guide tubes 315 and core wire 311 are embedded. Proximal to the proximal end of the plastic 305, a Luer fitting 348 (shown in FIG. 15) with access tube 346 provides access to the space between the injector tubes 316 and the guide tubes 315 through holes 347 in the guide tubes 315.

The distal sheath control handle 350 includes a distal portion 354 attached to the outside of the sheath 312 with Luer fitting 358 (shown in FIG. 15) and side tube 356 providing access to the lumen between the sheath 312 and the plastic 305 to allow it to be flushed with saline before the procedure begins. The handle 350 also has proximal portion 352 and elastic washer 359 that is compressed by screwing the proximal portion 352 into the distal portion 354 to lock the position of the sheath 312 onto the plastic 305. In this locked position with the INAS 300 closed as shown in FIG. 11 the INAS 300 is advanced into the body until the distal end with the marker band 324 of FIG. 11 is in the renal artery. The proximal portion 352 is then loosened so that the sheath control handle 350 can be pulled in the distal direction while holding the central guide tube handle 340 fixed. It is envisioned that when the proximal end of the sheath control handle proximal piece 352 touches the distal end of the outer portion 342 of the guide tube handle 340 as shown in FIG. 18, that the sheath 312 will be full retracted to allow expansion of the guide tubes 315 against the wall of the target vessel.

The full procedure for renal denervation using the INAS 300 is as follows:

1. Remove the sterilized INAS 300 from its packaging in a sterile field, flush the injection lumens 321 of the injector tubes and the space between the sheath 312 and plastic 305 and injector tubes 316 and guide tubes 315 with saline.
2. Access the aorta via a femoral artery, typically with the insertion of an introducer sheath.
3. Using a guiding catheter 80 of FIGS. 5A through 5E or a guiding sheath with a shaped distal end, engage the first targeted renal artery through the aorta. This can be confirmed with contrast injections as needed.
4. Place the distal end of the INAS 300 in its closed position of FIG. 11 into the proximal end of the guiding catheter. There is typically a Tuohy-Borst fitting attached to the distal end of a guiding catheter 80 to constrain blood loss.
5. The closed INAS 300 is then pushed through the opened Tuohy-Borst fitting into the guiding catheter.
6. Advance the INAS 300 through the guiding catheter, until the marker band 324 is distal to the distal end of the guiding catheter within the renal artery.
7. Pull the sheath 312 back in the proximal direction while holding the guide tube handle 340 fixed. This will allow expansion of the injector tubes 315 against the wall of the renal artery as shown in FIG. 15.
8. Lock the sheath control handle 350 down on the plastic 305.
9. Lock the Tuohy-Borst fitting at the proximal end of the guiding catheter down onto the sheath 312
10. Advance the guide tube handle 340 to be sure the distal ends 329 of the guide tubes 315 are in good contact with the wall of the renal artery and flaring outward in order to point more closely to perpendicular to the long axis of the renal artery wall.
11. While holding the guide tube handle 340 fixed, advance the injection handle 330 until its distal end touches the proximal end of the guide tube control handle 340. This will cause the needles 319 to advance through the distal ends 329 of the guide tubes 315 into the wall of the target vessel to the appropriate penetration limited by the two handles 330 and 340 touching.
12. Attach a syringe or injection system to the Luer fitting 338 that provides ablative fluid that will be injected into the wall of the renal artery. One could optionally inject an anesthetic drug like lidocaine and/or contrast media before the ablative fluid to prevent or reduce the pain associated with the procedure and/or ensure the needles are in the right position. It is also conceived that an anesthetic or contrast can be combined with the ablative fluid.
13. Inject an appropriate volume of the ablative fluid from the syringe or injection system through the lumens 321 of the injector tubes and out of the injection egress ports 317 into and/or outside of the wall of the renal artery. A typical injection would be 1-10 ml. This should produce a multiplicity of intersecting volumes of ablation (one for each needle) that should create a torroid of ablated tissue around the circumference of the renal artery as shown as the ablated regions shown in FIGS. 5D and 5E.
14. While holding the guide tube handle 340 fixed. Pull the injection handle 330 in the proximal direction retracting the needles 319 back into the guide tubes 315.
15. Unlock the sheath control handle 350 from the plastic 305 and while holding the guide tube control handle 340 fixed, advance the sheath control handle 350 in the distal direction until the guide tubes 315 are fully collapsed back into the distal end of the sheath 312 and the marker bands 327 and 324 are next to one another indicating that the INAS 300 is now in its closed position as shown in FIG. 11.
16. The same methods as per steps 6-15 can be repeated to ablate tissue around the other renal artery during the same procedure.
17. Remove the INAS 300 in its closed position from the guiding catheter. Being in the closed position, the needles 319 are doubly enclosed within the guide tubes 315 which are inside the sheath 312 so the sharpened needles 319 cannot harm the health care workers, or expose them to blood borne pathogens.
18. Remove all remaining apparatus from the body.

A similar approach can be used with the INAS 300, to treat atrial fibrillation through a guiding catheter inserted through the septum into the left atrium with the wall of the target vessel being the wall of one of the pulmonary veins.

Figure 19:
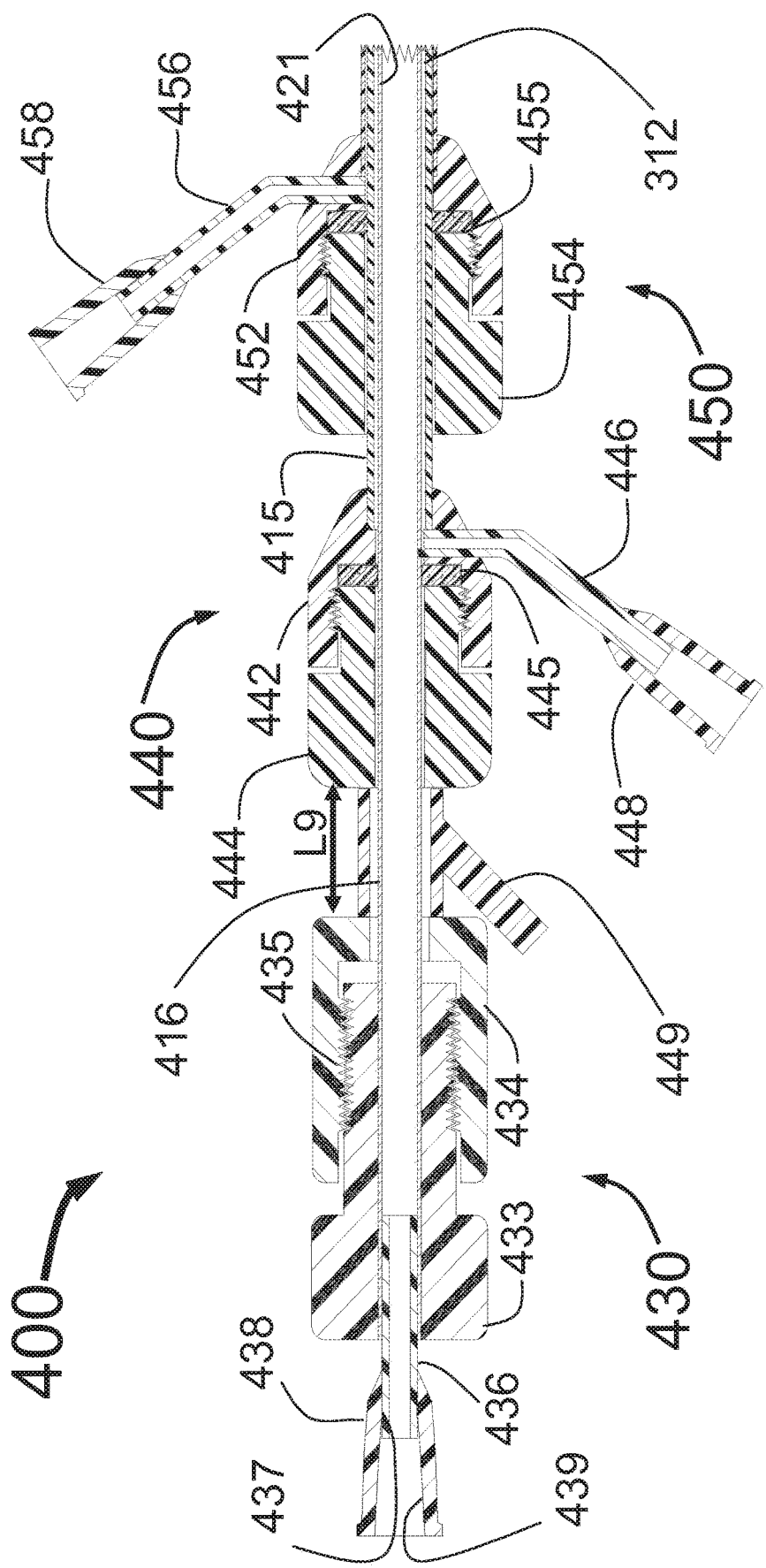
FIG. 19 is a longitudinal cross section of an alternate embodiment of all but the distal portion of the INAS using multiple guide tubes.

FIG. 19 is a longitudinal cross section of the proximal portion of an alternate embodiment of the INAS 400 which simplifies the design as compared to the INAS 300 proximal portion of FIG. 16. The INAS 400 uses the identical distal portion design as the INAS 300 of FIGS. 11-15. Three handles, the proximal injection handle 430, the central guide tube handle 440 and the distal sheath control handle 450 allow the relative longitudinal movement of the sheath 312, middle tube 415 and inner tube 416 with injection lumen 421. The position shown for FIG. 19 has the sheath control handle 450 near its most proximal position which would indicate the sheath 312 has been pulled back in the proximal direction. In this position, as with the INAS 300 of FIGS. 11-18 this will cause the distal portion of the guide tubes 315 to expand outward as shown in FIG. 14.

The gap with distance L9 between the injection handle 430 and the guide tube handle 440 can be adjusted using the screw adjustment piece 434 with screw threads 435 that allow it to move with respect to the proximal portion 433 of the proximal injection handle 430. The proximal end of the screw adjustment piece 434 is the penetration limiting member that will limit to the distance L9, the penetration of the needles 319 and injection egress ports 317 of the injector tubes 316 into the wall of the target vessel. Ideally, a scale can be marked on the proximal portion 433 of the injection handle 430 so that the medical practitioner can set the gap L9 and thus adjust the penetration distance. The central tube 416 with lumen 421 is sealed into the proximal piece 433 of the proximal injection handle 430. A luer fitting 438 with access tube 436 is the port for ablative fluid injection into the handle lumen 432. The lumen 439 of the Luer fitting 438 is in fluid communication with the lumen 437 of the access tube 436 which is in fluid communication with the injection lumen 421 of the inner tube 416. The inner tube 416 is typically a metal hypertube although a plastic tube or plastic tube with braided or helical wire reinforcement is also conceived.

The central guide tube handle 440 attached to and controlling the longitudinal movement of the middle tube 415 includes a proximal portion 444 that can screw into a distal portion 442. When screwed in to the distal portion 442, the proximal portion 444 will compress the washer 445 allowing the handle 440 to be locked down onto the middle tube 415. This is also needed during preparation for use when the Luer fitting 448 with side tube 446 can be used to flush the space between the inner tube 416 and middle tube 415 with saline solution.

The distal sheath control handle 450 attached to and controlling the longitudinal movement of the sheath 312 includes a proximal portion 454 that can screw into a distal portion 452. When screwed in to the distal portion 452, the proximal portion 454 will compress the washer 455 allowing the handle 450 to be locked down onto the sheath 312. This is also needed during preparation for use when the Luer fitting 458 with side tube 456 can be used to flush the space between the middle tube 415 and sheath 312 with saline solution.

A removable spacer 449 that prevents advancement of the injection handle 430 will help ensure that the needles are not accidentally advanced before the INAS 400 is on its open position inside the renal artery. It is also conceived that the handles can be color coded or numbered to facilitate the proper order of use. For example the sheath control handle labeled "1" is pulled back first the spacer 449 labeled "2" is removed and then the injection handle 430 labeled "3" can be advanced.

Figure 20:
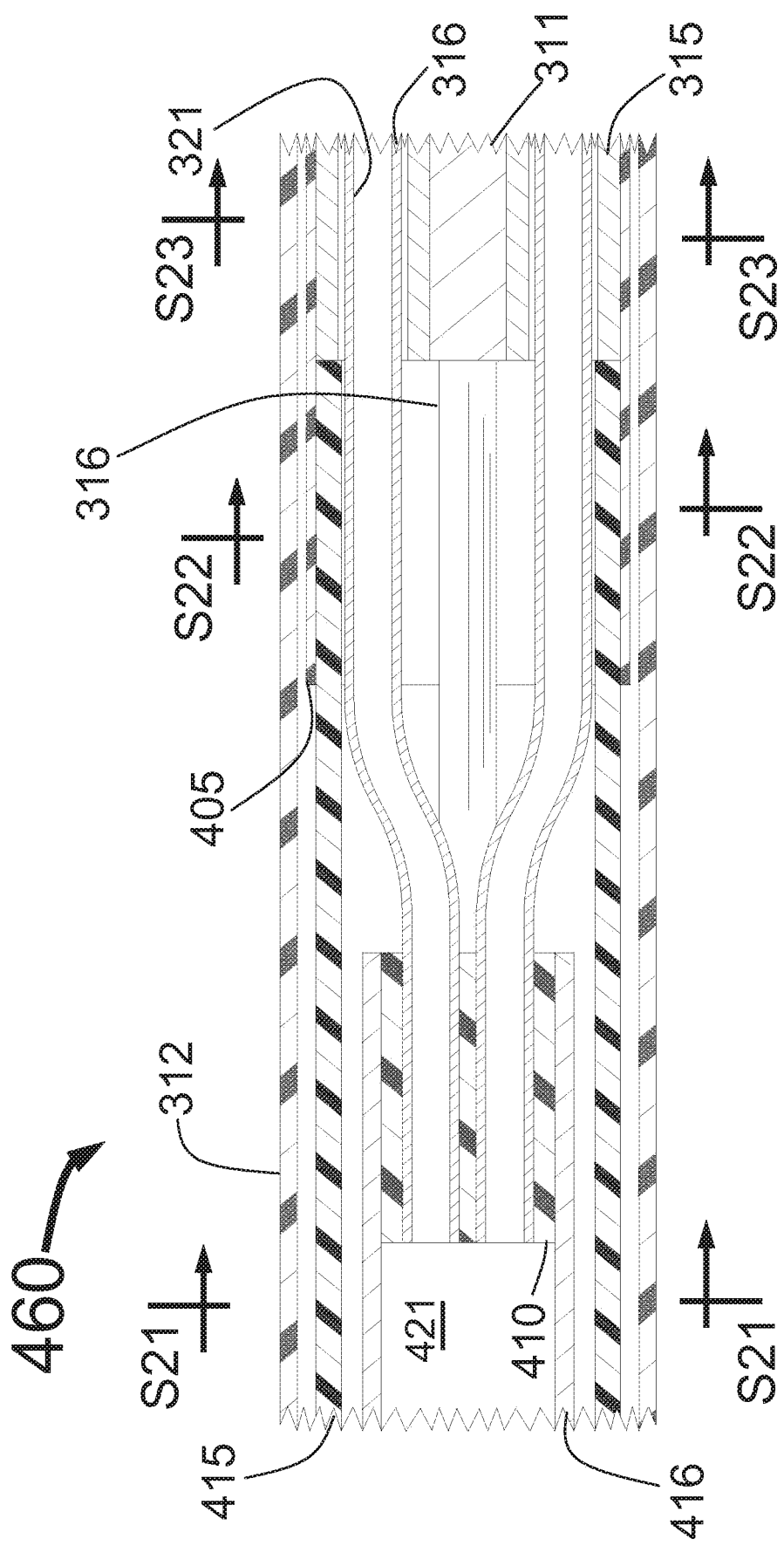
FIG. 20 is a longitudinal cross section of a central transition portion connecting the proximal portion of the of the INAS of FIG. 19 with the distal portion of the INAS of FIGS. 11-14.

FIG. 20 is a longitudinal cross section of a central transition portion 460 connecting the proximal portion of the INAS 400 of FIG. 19 with the distal portion of the INAS 300 of FIGS. 11-15. The proximal end of the central transition portion 460 includes the same three concentric tubes located at the distal end of the handle portion of the INAS 400 shown in FIG. 19. Specifically, the proximal end of the transition portion 460 includes the inner tube 416 with injection lumen 421, the middle tube 415 and the sheath 312. At the distal end of the inner tube 416, a manifold 410 is inserted which seals the inner tube 416 to the four injector tubes 316 such that the lumen 421 of the inner tube 416 is in fluid communication with the lumens 321 of the four injector tubes 316. In addition, longitudinal motion of the inner tube 416 will therefore be translated to longitudinal motion of the four injector tubes 316.

The middle tube 415 seals inside of the plastic member 405 which also seals to the guide tubes 315 and core wire 311. Longitudinal motion of the middle tube 415 will translate into longitudinal motion of the four guide tubes 315. The sheath 312 is the same sheath as in the distal portions of the INAS 300 of FIGS. 11-15.

FIG. 21 is a circumferential cross section at S21-S21 of the central transition section 460 of FIG. 20. Looking in the distal direction, one sees in cross section, the three concentric tubes the sheath 312, middle tube 415 and inner tube 416. Inside the inner tube one sees the proximal end of the manifold 410 and the proximal ends of the four injector tubes 316. It can clearly be seen that the manifold 410 seals the four injector tubes 316 into the inner tube 416 and the lumens 321 of the injector tubes 316 open into the lumen 421 of the inner tube 416.

FIG. 22 is a circumferential cross section at S22-S22 of the central transition section 460 of FIG. 20. Looking in the distal direction one sees in cross section, the sheath 312 and middle tube 415. The middle tube 415 is sealed into the distal portion of the plastic member 405. One also sees the proximal end of the four guide tubes 315 and core wire 411. It also shows how the four injector tubes 316 enter the proximal ends of the guide tubes 315.

FIG. 23 is a circumferential cross section at S23-S23 of the central transition section 460 of FIG. 20. This cross section is identical to the circumferential cross section shown in FIG. 13 showing the sheath 312 and plastic member 405 (was 305 in FIG. 13) that seals and attaches together the four guide tubes 315 and the core wire 311. The injector tubes 316 lie concentrically inside of the four guide tubes 315. Thus, FIGS. 20-23 clearly show how the simplified proximal end of FIG. 19 connects to the distal portion of the INAS 300 of FIGS. 11-15.

Figure 24:
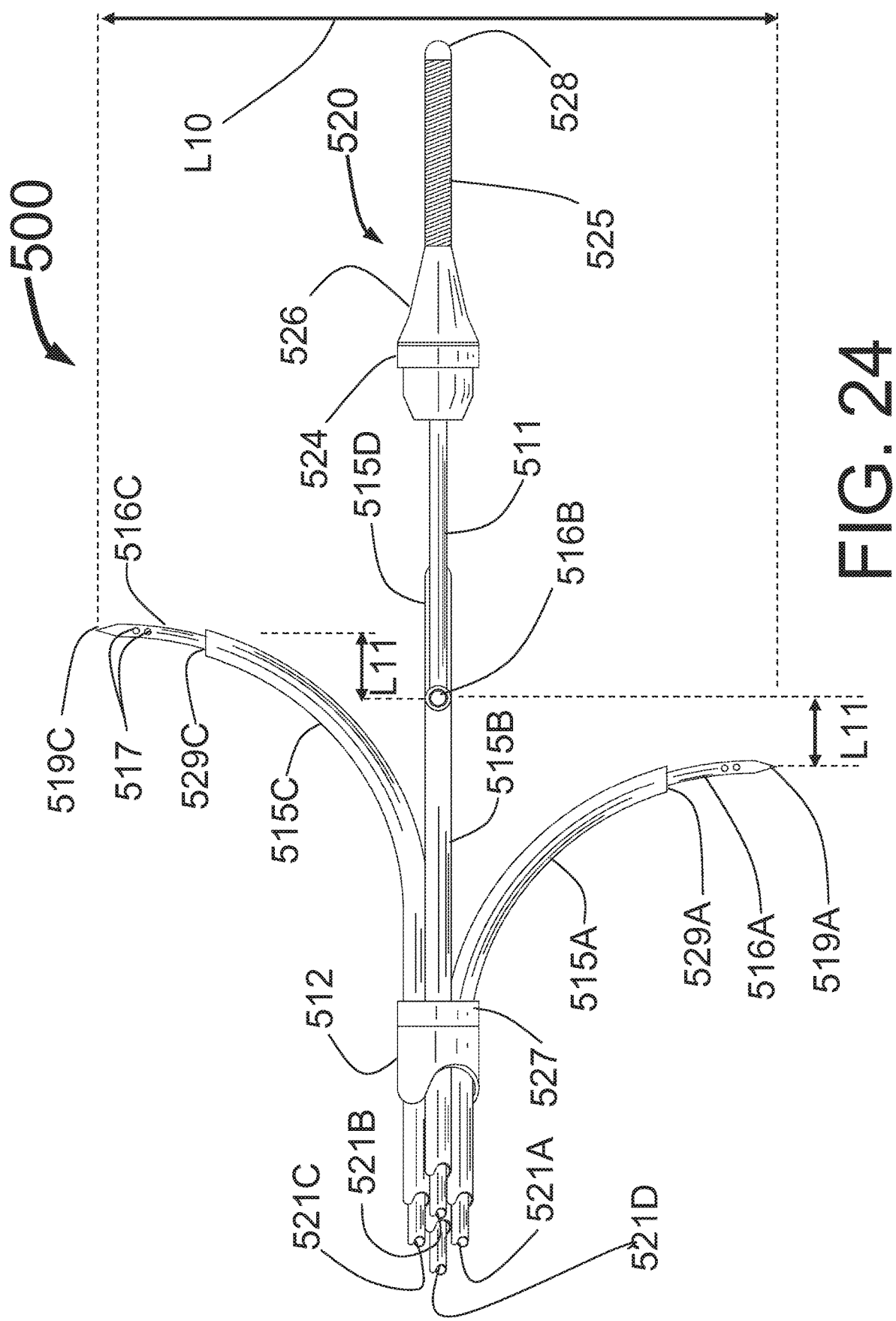
FIG. 24 is a schematic view of the distal portion of another embodiment of the INAS having longitudinally offset injection egress locations to allow helical (spiral) chemical nerve ablation.

FIG. 24 is a schematic view of yet another embodiment of the distal portion of the present invention Intravascular Nerve Ablation System (INAS) 500 in the fully open configuration with the injection tubes 516A, 516B, 516C and 516D (516A-D) shown advanced beyond the distal end of the guide tubes 515A, 515B, 515C and 515D (515A-D) respectively. The distal end of the injector tubes 516A-D have the sharpened needles 519A-D with injection egress ports 517.

In this configuration the sheath 512 has been pulled back to allow the guide tubes 515A-D to expand outward. The guide tubes 515A-D are typically made from a memory metal such as NITINOL. The injector tube 516A-D may be made from any metal such as titanium, stainless steel, NITINOL or a radiopaque metal such as tantalum or platinum. If the elements 515A-D and/or 516A-D are not fabricated from a radiopaque metal it is envisioned that distal portion of the injector tubes 516A-D and guide tubes 515A-D could be coated with a radiopaque material such as gold, typically at or near the distal end of the tube(s) or a piece of radiopaque material may be used to form or be located near the sharpened needles 519A-D at the distal end of the injector tubes. The diameter L10 denotes the memory configuration for the fully open guide tubes 515. For use in the renal arteries, L10 would typically be between 5 and 10 mm with 8 mm being a best configuration if only one size is made as very few renal arteries are larger than 7 mm diameter. Also shown in FIG. 24 are the distal ends 529A-D of the guide tubes 515A-D that in the fully open configuration are approximately parallel to the longitudinal axis of the INAS 500'. The distal portion of the INAS 500 has the tapered section 526 attached to the fixed guide wire 520 with tip 528, outer layer 525 and core wire 511. The significant difference between the INAS 500 of FIG. 24 and the INAS 300' of FIG. 14 is the longitudinal offset between the distal ends 529 A-D of the guide tubes 515A-D which will cause the injection egress points associated with each of the injector tubes 516A-D to be offset in the longitudinal direction. The longitudinal offset distance L11 is shown between adjacent injector tubes 516A and 516B and between 516B and 516C. The longitudinal offset difference L11 can be as small as 1 mm and as long as 25 mm although the most desirable offset would be between 5 mm and 10 mm is envisioned. The advantage of the longitudinal offset that creates a helical ablation pattern is to reduce circumferential injury to the artery to prevent vessel failure or late vascular contraction that is seen in balloon angioplasty from scar tissue formed in the arterial tissue. The offset ablation of the INAS 500 will still substantially ablate the sympathetic nerves with less potential risk of late complications from negative arterial remodeling. The helical pattern of ablation has been shown to work in studies of RF ablation and should therefore also work with injection of an ablative solution.

While the INAS 500 shows four injector tubes 516A-D, it is envisioned that as few as two and as many as eight injector tubes with injection egress can be used. The preferred embodiment for renal denervation is three or four.

While this description has focused on use of the INAS for use in ablation of tissue, it is also clearly envisioned that the apparatus and methods of FIGS. 1-23 can be applied to the use of this apparatus to inject any fluid for any purpose including that of local drug delivery into a specified portion of a blood vessel or the volume of tissue just outside of a blood vessel.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. An intravascular nerve ablation system for delivery of an ablative fluid to a volume of tissue in proximity to a vessel wall of a target vessel comprising:
   a catheter body having a central axis;
   at least a first guide tube and a second guide tube, each guide tube having a distal end and a central lumen, each guide tube having a distal portion that is movable between a first position aligned with the central axis and a second position inclined away from the central axis, wherein the first and second guide tubes are configured to slide distally relative to the catheter body to an open configuration until the first and second guide tubes are prevented from further distal movement by a single guide tube stop near a proximal end of the system, wherein the first guide tube intrinsically curves laterally outward from the central axis and the second guide tube intrinsically curves laterally outward from the central axis;
   at least a first injector and a second injector, the first and second injectors located coaxially inside of the first and second guide tubes respectively, wherein the distal ends of the first and second guide tubes are configured to press against, but not penetrate, the vessel wall of the target vessel as the first injector and the second injector are advanced into the volume of tissue; and
   wherein the first injector and the second injector are configured to advance relative to the first guide tube and the second guide tube, respectively, until the first injector and the second injector are prevented from forward movement relative to the first guide tube and the second guide tube by a single injector stop near the proximal end of the system, the first and second injectors pre-shaped to parallel a curved distal shape of the first and second guide tubes to enhance coaxial movement of the first and second injectors within the first and second guide tubes.

2. The system of claim 1 where the first injector and the second injector are coupled for simultaneous movement.

3. The system of claim 1 where a proximal section of the intravascular nerve ablation system includes a port in fluid communication with the first and second injectors.

4. The system of claim 1 where a depth of penetration of the first and second injectors into the vessel wall of the target vessel is preset during manufacturing.

5. The system of claim 1 further including an injection handle located near a proximal section of the intravascular nerve ablation system, the injection handle further adapted to control distal and proximal movement of the first and second injectors.

6. The system of claim 1 further comprising a guide tube handle located near a proximal section of the intravascular nerve ablation system, the guide tube handle further adapted to control distal and proximal movement of the first and second guide tubes.

7. An intravascular nerve ablation system for delivery of an ablative fluid to a volume of tissue in proximity to a vessel wall of a target vessel comprising:
   a catheter body having a central axis;
   a first guide tube having a first distal end and a central lumen, the first guide tube having a distal portion adapted to move outward, wherein the first guide tube intrinsically curves laterally outward from the central axis;
   a first injector, a portion of the first injector located coaxially inside of the first guide tube, the first injector being adapted to slide in distal and proximal directions within the first guide tube;
   a second guide tube having a second distal end and a central lumen, the second guide tube having a distal portion adapted to move outward, wherein the second guide tube intrinsically curves laterally outward from the central axis;
   a second injector, a portion of the second injector located coaxially inside of the second guide tube, the second injector being adapted to slide in the distal and proximal directions within the second guide tube;

wherein the first distal end of the first guide tube and the second distal end of the second guide tube are configured to advance to rest against the vessel wall of the target vessel without penetrating the vessel wall of the target vessel, wherein the first guide tube has a first proximal end and the second guide tube has a second proximal end, wherein the first proximal end and the second proximal end are coupled to a central member thus forming a fixed end, wherein the central member is slidable along the central axis of the catheter body to move the first guide tube and the second guide tube relative to the catheter body, wherein the first distal end is cantilevered from the first proximal end and the second distal end is cantilevered from the second proximal end such that the first distal end and the second distal end are not connected along the distal portions of the first guide tube and the second guide tube thus forming free ends;

wherein the first injector and the second injector are configured to advance beyond the first distal end of the first guide tube and the second distal end of the second guide tube, respectively, to penetrate the vessel wall of the target vessel until a depth of penetration of the first injector and the second injector into the vessel wall of the target vessel is limited, the first and second injectors pre-shaped to parallel a curved distal shape of the first and second guide tubes to enhance coaxial movement of the first and second injectors within the first and second guide tubes.

8. The system of claim 7 where the first injector and the second injector are coupled for simultaneous movement.

9. The system of claim 7 where the depth of penetration of the first and second injectors into the vessel wall of the target vessel can be adjusted by the user to increase or decrease the depth of penetration.

10. The system of claim 8 where the intravascular nerve ablation system includes a scale to facilitate adjusting the depth of penetration of the first and second injectors into the vessel wall of the target vessel.

11. The system of claim 7 further including a handle which includes a port in fluid communication with the first and second injectors.

12. The system of claim 7 where the depth of penetration is preset during manufacturing.

13. An intravascular nerve ablation system for circumferential delivery of an ablative fluid to a volume of tissue in proximity to a vessel wall of a target vessel comprising:
a catheter body having a central axis;
a first guide tube having a first distal end and a first central lumen, the first guide tube having a first distal portion adapted to move outward such that a first distal surface of the first guide tube comprises a blunt distal tip, wherein the first guide tube intrinsically curves laterally outward from the central axis;
a first injector, a portion of the first injector located coaxially inside of the first guide tube, the first injector being adapted to move in distal and proximal directions within the first guide tube;
a second guide tube having a second distal end and a second central lumen, the second guide tube having a second distal portion adapted to move outward such that a second distal surface of the second guide tube comprises a blunt distal tip, wherein the second guide tube intrinsically curves laterally outward from the central axis, and the first and second guide tubes are configured to not penetrate the vessel wall;
a second injector, a portion of the second injector located coaxially inside of the second guide tube, the second injector being adapted to move in the distal and proximal directions within the second guide tube; and
wherein the first injector and the second injector are configured to advance relative to the first distal end of the first guide tube and the second distal end of the second guide tube, respectively, to penetrate the vessel wall of the target vessel, the first and second injectors pre-shaped to parallel a curved distal shape of the first and second guide tubes to enhance coaxial movement of the first and second injectors within the first and second guide tubes.

14. The system of claim 13 where the first injector and the second injector are coupled for simultaneous movement.

15. The system of claim 13 where the first guide tube and the second guide tube are coupled for simultaneous movement.

16. The system of claim 13 where a depth of penetration of the first and second injectors into the vessel wall of the target vessel can be adjusted by the user to increase or decrease the depth of penetration.

17. The system of claim 13 where the intravascular nerve ablation system includes a scale to facilitate adjusting a depth of penetration of the first and second injectors into the vessel wall of the target vessel.

18. The system of claim 13 where a proximal portion of the intravascular nerve ablation system includes a port in fluid communication with the first injector and the second injector.

19. The system of claim 13 where a depth of penetration of the first and second injectors into the vessel wall of the target vessel is preset during manufacturing.

* * * * *